US011124777B2

United States Patent
Chen et al.

(12)

(10) Patent No.: US 11,124,777 B2
(45) Date of Patent: Sep. 21, 2021

(54) ATTENUATED PORCINE SAPELOVIRUS STRAIN AND IMMUNOGENIC COMPOSITIONS THEREFROM

(71) Applicant: Iowa State University Research Foundation, Inc., Ames, IA (US)

(72) Inventors: Qi Chen, Ames, IA (US); Bailey Arruda, Ames, IA (US); Kent Schwartz, Ames, IA (US); Phillip Gauger, Ames, IA (US); Jianqiang Zhang, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 16/702,287

(22) Filed: Dec. 3, 2019

(65) Prior Publication Data

US 2020/0172878 A1    Jun. 4, 2020

Related U.S. Application Data

(60) Provisional application No. 62/774,511, filed on Dec. 3, 2018.

(51) Int. Cl.
| | |
|---|---|
| *C12N 7/00* | (2006.01) |
| *A61K 39/125* | (2006.01) |
| *C07K 16/10* | (2006.01) |
| *A61K 39/00* | (2006.01) |

(52) U.S. Cl.
CPC .............. *C12N 7/00* (2013.01); *A61K 39/125* (2013.01); *C07K 16/1009* (2013.01); *A61K 2039/5254* (2013.01); *A61K 2039/545* (2013.01); *A61K 2039/552* (2013.01); *A61K 2039/55511* (2013.01); *A61K 2039/55561* (2013.01); *C07K 2317/24* (2013.01); *C07K 2317/31* (2013.01); *C07K 2317/35* (2013.01); *C07K 2317/54* (2013.01); *C07K 2317/55* (2013.01); *C07K 2317/565* (2013.01); *C07K 2317/622* (2013.01); *C07K 2317/626* (2013.01); *C12N 2770/32021* (2013.01); *C12N 2770/32034* (2013.01)

(58) Field of Classification Search
None
See application file for complete search history.

(56) References Cited

U.S. PATENT DOCUMENTS

2020/0172878 A1*   6/2020   Chen ..................... C12N 7/00

OTHER PUBLICATIONS

SEQ ID No. 2 alignment with Geneseq db access No. BHV21858 by Chen et al. Jul. 2020 in USPgPub 2020172878.*
Horak et al. ("Porcine sapelovirus. 2016; Swine Health Information Center and Center for Food Security and Public Health.").*
Malik et al. ("Sapelovirus." Emerging and Transboundary Animal Viruses. Springer, Singapore, 2020. 345-355).*
Chen, et al., "Complete Genome Sequence of Porcine Sapelovirus Strain USA/IA33375/2015 Identified in the United States", Genome Announcements, American Society for Microbiology, vol. 4, Issue 5, 2 pages, Published Sep. 29, 2016.
Chen, et al., NCBI GenBank KX574284, 5 pages, submitted Jul. 15, 2016.

* cited by examiner

*Primary Examiner* — Shanon A. Foley
(74) *Attorney, Agent, or Firm* — McKee, Voorhees & Sease, PLC

(57) ABSTRACT

The present invention is directed to novel nucleotide and amino acid sequences of Porcine *Sapelovirus* ("PSV"), including novel genotypes thereof, all of which are useful in the preparation of vaccines for treating and preventing diseases in swine and other animals. Vaccines provided according to the practice of the invention are effective against multiple swine PSV genotypes and isolates. Diagnostic and therapeutic polyclonal and monoclonal antibodies are also a feature of the present invention, as are infectious clones useful in the propagation of the virus and in the preparation of vaccines. Particularly important aspects of the invention include polynucleotide constructs that replicate in tissue culture and in host swine. The invention also provides for novel full-length PSV genomes that can replicate efficiently in host animals and tissue culture.

18 Claims, 6 Drawing Sheets

Specification includes a Sequence Listing.

>PSV/US/ISU26908B/18-spinalcord (SEQ ID NO: 1)

GGGGTACATGCGTATTACGGTACGCATGTATTCCACACTCATTTCCCCCCTCCA
CCCTTAAGGTGGTTGTATCCCCATACCTCACCCTCCCTTCCACACAGGACGGAT
ACTTGGACTTGGACCCACGGCGAGAACATATGGTATGGCTTTTGGATACGGAT
GAATGGCAGTAGCGTGGCGAGCTATGGAAAAATCGCAATTGTCGATAGCCATG
TTAGTGACGCGCCTCGGCGTGCTCCTTTGGTGATTCGGCGACTGGTTACAGGAG
AGTAGGCAGTGAGCTATGGGCAAACCTCTGCAGTATTACTCAGAGGGAATGTG
CAATTGAGACTTGACGAGCGTCTCTTTGAGATGTGGCGCATGCTCTTGGCATTA
CCATAGTGAGCTTCCAGGTTGGGAAACCTGGACTGGGCCTATACTACCTGATA
GGGTCGCGGCTGGCCGCCTGTAACTAGTATAGTCAGTTGAAACCCCCATGGA
ATCTACTACTACTCTTTCATTTGCAACTGGATCCCTAAGAAACAGAGAGCCCG
TGTGTACCTTACCACCAGTGTAACACACGAGAAATCAAGTGGACCCTACACAT
ATGTAGTGTCTGACATGATCATGAAAGAAAACAGTAGAACCTCCCTTGCTATG
GCTTTCGTAGAAGGGAAGACACTTGTGTTCAACACCGGCACACAATTGGGACA
AGTTCATTCAGCTAACACAGGCAATAAACCTCAAGGAGCATACAACCATGGCT
CCGGTAGTATTACACAAATAAACTACTATGGTTCTGATTACTCCCAAGCATGG
AATCCTACACAACAGCAAATGGACCCCTCCCAGTTCACCAAACCAGTGACTGA
AATAGCCAATGCAATGGCAGGACCATCTCTCAAGGCACCTGACAAGGAAGAA
GAAGGGTACAGTGATAGGTTAATGCAATTGACAGCAGGAAACTCCTGTATAAC
AACACAAGAAGCAGCTAAAGCAGTTGTAGCATATGGACAATGGCCAAGTTAT
AACATAGATGCAGGAGAACATCTAGATCTTGCTACAACTCCAGGGACAGCAGT
GGACAGGTTTTACACCTTTGACAGCTTAAGATGGACCGACACACAAGTCGGTG
AATGGTCTCTGCCACTGCCTGGTGGTTTGATGGACACAGGCGTGTTTGGTCAAA
ACCTAAGATTCCACTACCTCTCCAGGATGGGCTTTTGTGTACATGTACAGTGCA
ATGCATCAAAATTCCACCAGGGTGCACTCATAGTTGCAATGATACCAGAGCAT
CAAACACCTACCCAAGTGAGTAACGGGTTTGAGTATAGAAGTGGAGTGACCTA
CCAGGGAAACAATTATCCAACTGAACAACTACCTATATTCCACACCAGATTA
TAAACCTGAGGACCAACAACTCTGCAACAATAGTCTATCCATATACCAATTGT
ACTCCAGCAGGATTTGGTTTAGCACACAACTTTGTCACCCTGGTTATTAGGGTT
TTAGTGCCACTCAAGTACAATACAGGTGCTTCAACTTTTGTTCCTATTACTGTT
AGTGTGGCCCCAATGTGTTCACAGTTTGCAGGATTGAGATCAGCAGTAACAAG
ACAGGGTTTTCCTGTTAGGCAGGTACCAGGCAGCCAACAATTTATGACAACAC
AAAGAGATAGTGGGATACCAATCTACCCAGAGTTTCAGAAAACCCATAATTTC
AAATTGCCCGGAAGGGTAACCAATTTGCTACAAGTTGCTCAGGTGGGGACCTT
TCTCAAATTTAGTAATTCTACAAACGACACCAATAGAATCTATTTGAATTTGGA
TATTACACAGGGTGACCAGTCATCAAGGATGGTGGCTATTGATGTTAGCATGG
TTTCAGCCCACTTGTCCACCACATACCTTTCACGGTTGGCACAGATGTATGCCA
ATTACAGGGGTTCTGTTGTTTTTGAGTTTATGTTTTGTGGTAGCCAGATGGCCA
CTGGGAAACTACTGATAGCATACACACCTCCTGGTGGCACTTCCCCCACAACT
AGGACTGATGCAATGTTGGCAACACATGTTATTTGGGATATAGGTTTACAGTC
CACATGTAAAATGGTGGTCCCTTACATATCATCATCACAGTACAGACAGAACA
ATTTGACCCAAACAACACTATCTTACAATGGGTGGGTGACCATATTTCAACAG
ACGGCACTAGTTGTACCCCCTGGAGCCCCATCGACTTGCCAGTTAGTTGCCACC
GTGAGTGCAGCAGATAACTTTGTTCTTAGGATTCCCACAGATACCACATATTTT
GCTGATTATCAGGGTGATGTAAAAGATGTTGTACAGGCAAGCATAAATACCAC

*FIG. 1A*

```
CTTGCAAAATGCACTAAACACGAGACCACAGCAGGAACAGTCATCAAATGGT
ATAATGGTTAATCAAGGGGACGCACCTGCATTAACAGCGGCTGAGACTGGTGA
GTCTGATACTAATTCTGGTGGATCAACAATGGAACTTCAAGCAACAAACTGTG
TGTTTAGCCTAAGAGAAACAGATTTAGAGTACCTAATGTCTAGATATTCACTTA
TGTTTGAGGGCACTTTGGATTACACTGATGGGGCTGGCAAAAGGCATTTGAGG
TATGATTTGAATTTTAGACAAATTGGCAAATCAGGTAGTGATATTACCAAATTT
AAGGCTTTTACATACTGGAGGTTTGATTTAGATGCTGTGGTAATGATACTGGAG
GACAAGCCCGCAGCAGTGAGGAACCTTATGTTTCAGATTTTGTTTACCCCCCAT
GGGGGTGCTATACCTGGTACACATAACTCCCAGATTTGGAATGCTCCTAATTCA
ACCAGTATTTACACCAGAGTAGGAAATTGTCCTGCCTCGTTTAGGATACCTTTT
ATGTCTGTTTGCAATTATTATACTTCCTTTTATGATGGTGATGGGAATTTTGATA
TGAATGGTGCGTCTTATGGTATTAATCCAGGTGATTTTATAGGCACAATATCTA
TTAGGATGGCCAATGACTTTTTTACTAATACTACCACTGGTTCCTTTAGAGCTA
AGATCTTTCTTAGGCCTGTAAATATTGAAGCCTATATGCCTAGACCTCTTATTT
CCTACAAGGCTAATGGTGATGCCAGACAAGATAGTTCACAATACTACCCTGCA
GCCCAGACGGGGTTTTACCCCGCGGAACAGCTGGGACCCTATGAAATTTGCCA
AACCAGACATGCTTCAGAGCTAATTGATACTAAATGGGCAAGATACTCTTGCT
CGGTTAAATTTGACAGAGGTTCATTTACAGCATGGTTTGTGGGAGAAGACCTG
CTTTTGGTACCCTACCATGCTGCAAACAATTGGAGTCAGACAACACATGTGTTC
CTGTGGAGAGCATGGGATAAGGACTGGAGAGACCATCCTGAATTGGAAATGA
AGATCCCCATTTTGGACATGTGGACTGATTCTACCAGAGATGTCACTTTTCTTA
AATTGGCCTACGCTACACCATACTGGTTGGAGATGCCAGCAAAAGGTTCTGCC
ATAGGTGATTACATTGTAGTTGTGAATTCAGCCCACTTCCCATGGAAACAGTAC
TCAGGCCCAAAACCATTTAGACACCCCTACTTACATATTGGACAACATACCCA
ATACAGACTGTGGATGCATGCTGGTGATGCTGACAATGGCTTCTGTGGAGCCG
GTTTAATATCTAGAGGTAAACTTTATGGTATAGTTACAGCAAGGACAGAGGCT
AAATCAGGTGGTACCTATGTGGCCTACACTGAACTGGATGAAGATACCTTCCT
ACAAACACAACAAAGATGTTTTGATTTTGGAATGGATTCACACTTCAATCTTGG
AATGCATGACTGGGTCCAGGGACTCGGCCAGGTGTTCGGAGAGGGTGTTTCTG
GGGAGGTGAAAAGACAAGTGGAAGATTACTTAGGCCAGATCAAGCCCATTATT
GATTCAGGTACCAATAAAATTAAGGATGTTATTAAAGATGAAATGGTTAGTGC
CAGTATGTCCTTGTTAGTTAAGGTAGTTGCTTCCCTAGTACTGTATATGAATTCT
AAGGATGACTGTAAAATGTCCACTTTAGCTTCATTGGGTGCCCTTTTAGGTGTA
GATATATTTTTGACTGATCCTATTATGTACCTGTATAGTAAGATAACTGGAGAA
CCTCACAGACAGGGGCCAACAGAGTGGCTTAAAGAGTTCAATACAGCCATAA
ATGCATTTAAAGGATTTGATTTTCTCTGCTCCAAATTAATGCAATTGATTGAAT
GGATTAAACAGTTTTCCAGAGGGTTGAACCAGAGTACAAGGAGTTTAAGGAG
TTACTTGAATCTTGGCCCAAAGTTTGTGCCAAAGTGTTGGAGTTTAAGAACTGC
AAAACAACACTAGGACAAGAAGATATTTGTCAAATAAAGGTTTACATAGACA
AAATGATTGAGTTGGGAAACAAATATGGCCACAAATTTCATTTACAGATGTCT
CAGTTACTGCAATGTTCAAACATAATAAACAAAGCTTACAGTAACATGACAAG
ATCTAGACATGAACCTGTTGCAATTCTTATACATGGTGCTCCTGGAACTGGAAA
GTCACTTGCTACAGAAATAATTGGTAGGGCAATAGCAGATAAGTTAGATAATC
AGAGACCTTACACACTCCCACCAGACCCCAAACATTTTGATGGATATAATCAA
CAGAAAGTGGTTATTATGGATGATTTAGGACAAAACCCAGATGGTGAAGATTG
CAAGATGTTTTGCCAGATGGTGTCAACCACTACTTACATTCCACCTATGGCCTC
CTTAGATGAGAAAGGACTTCCCTTTATTTCTGACTTTGTTCTTGCTTCTACTAAC
CAGCATGCTTTGACCCCCAGAACTATTGCTGAGCCTGATGCTATTAATAGAAG
```

FIG. 1B

```
ATGGTTTATGAATGTAGATATTCACCTTAAGAAAGAATACAAGGATGATAGAG
GAAGGTTAGACATGTCAAAGTGTTTGCCTTGTAAAGATTGCAAACCAGTGAAT
TTCAGGAGATGTAACCCATTGATTTGTGGAAAAGCCATCATTTTACTGGACAG
GAAAACCCAGAAAAACTGGACCCTTGATTCAGCAGTTAGTTACTTATTGGATG
AATCAGAGAGAAGAAAAGGGTTCTTAAATGTAGTGGATGCAATCTTTCAGGA
CCTGTGCAGATTCCAGAATGTGTTAGAGAGGATGAACTGAAGAGGAAGAAGG
TGAATTCAGAGAGAGACATCCAAGCTGATGTGATGGAATTAGTTAGATGTACA
AAATCCCCTGTTATAATTGAGGAATTAGAGAAAGCAGGTTTCATCATTCCTGTT
GAGGCAGAAGTGATTAGACAGACTAGTAATGTGAATAATGTAACCCAAATTAT
TTCAGCAACTCTAGCTAGTTTGGCAGCTATAATTTCTGTAGGGACTGTAGTTTA
TTTAATGGTTAAGTTGTTTTCCACAAAACAAGGAGCATACACTGGTGTGCCCA
AACCAGAAACCAAGAGACCTGTACTTAGAAAAGCAGTAGTGCAGGGCCCAGA
CATGGAATTTGCCAAGTCAATTATGAGATCAAATCTGTGTCAGGTAACCACCA
GTGTGGGACCCTTTACCGGGCTGGGCATCTGTGATAACATCTTGGTGCTACCAC
GACATGCTTATGTGAGTGGAAACATAGTGTTAGATGGTATAGACATTCCTGTA
ACAGATGCTGTAGAATTAGAAGCAGAGGAGGGAAATTTGGAATTAGTACAGTT
AACCCTTAAGAGAAATGAAAAATTTAGGGATATTAGAAAGTTTTTAAGTAATG
GTTTTCACAGTGAGAATGATTGCTGGTTGTGCATTAATTCTGAGATGTTTTCTA
ATGTATATACCTCTTAAGAGTGTTTCTGCCTTTGGATTCCTTAACCTTTCTAT
GACTCCTACTTACAGAACACTTGTTTACAATTACCCTACCAAGATGGGACAAT
GTGGTGGTGTTGTGCTGAAAGCAGGAAAGATTTTAGGCATACATATTGGTGGT
GATGGAACCAGAGGGTTTGCAGCCCTACTGAAGAGAGATTACTTTGTAAACAA
ACAAGGTTTGATAACAGAGAGATACACACCATCAAGACCTATTAATGTTAGAA
CAAAGACAGCTTTCCAACCTTCTGTTTTTCATGATGTCTTTCCTGGGAGTAAGG
AACCTGCAGCAATGAGTGTGCATGATCCAAGACTTGAAGTGGATCTGGAAGAA
GCAATATTTGCAAAGTACAAAGGCAATGTTGACACCACACTTCCAGAAGAAGC
ACTTATAGCAATTGACCATTTGGTTTCCAAATTTAAGGCAATTGTACCAGACAA
TCTGTGTGAGAAGATGTCATTGGAGGATGTTGTCTATGGTACTGATAATCTGGA
TGGACTAGATTTAACCACTTCAGCAGGTTACCCCTACAACACCTTGGGGATTA
GAAAGAAAGATCTTATTCCTCCCAAAGGACAGTCTCTTTCCCCTCTTATAAAGG
CTCTTGATCTTTATGGATATGATTTACCCTTTACTACTTACATGAAGGATGAGTT
GAGACCAAAGGAGAAAGTGAAGATGGGCAAAACCAGGGTCATTGAGTGTTCA
TCACTTAATGATACCATAATGATGAAGCAGACTTTTGGTCATCTGTTCCAGACA
TGCCACAAGAATCCTGGAACCTACACTGGTGTAGCTGTAGGCTGCAACCCAGA
TGTGGATTGGTCAAAGTTTGCTGCTGAGATTGGTGATGCCTATGTGTGTGCTTT
TGATTATACAAATTGGGATGCTAGTCTGTCACCTTTGTGGTTTGATGCTTTAAA
GTTGTTTCTTTCCAAACTAGGTTACAGTGGTAGGGATTTAGTTTTGATTGATCA
GTTGTGTTATTCAAATCACATTTACAAGAATAAGGGATACAAAGTTACCGGCG
GTATGCCATCTGGTTGCTCCGGAACTAGTATCTTTAATAGCATTATTAACAATA
TAGTTATTAGGACTTTAATAATGTTAGCATATAAGAATATTAATTTAGATGAGT
TGTTAGTTTTATGTTATGGTGATGATTTATTGGTTGCCTATCCCTATGAATTAGA
TCCAAATGTGCTGGTTCCATTGGCAAAGAGTTATGGTTTGACCATAACACCAG
CAGACAAATCAACAACTTTCCAAACAGGAACAAAGTTAACAGATGTTACCTTC
CTGAAGAGGGGTTTCAAATTCGATGAGGAATACCCCTTCCTGTGTCATCCTGTA
TTTCCTATGGAGGAGGTGCATGAATCAATTAGATGGACCAAGAATGCCAGCTA
TACCCAGGAACATGTTACATCGCTGTGTCTTTTGGCATGGCACAATGGTGAGG
AGGTTTATGAAGAGTTCTGTACGAAAATCAGATCAGTTCCAGTAGGCAGAGCT
CTCATATTACCACCTTACTCTCAGCTGCGTAGGTCTTGGTTAGATATGTTTTAG
GCGGCGTGAACATATCAGTGATACAGGATTAACAATTAGGCTAATTGGCAATA
GACCCTAAGCCGCCTATAGGG
```

FIG. 1C

>PSV/US/ISU26908B/18-P7ST (SEQ ID NO: 2)

GGGGTACATGCGTATTACGGTACGCATGTATTCCACACTCATTTCCCCCCTCCA
CCCTTAAGGTGGTTGTATCCCCATACCTCACCCTCCCTTCCACACAGGACGGAT
ACTTGGACTTGGACCCACGGCGAGAACATATGGTATGGCTTTTGGATACGGAT
GAATGGCAGTAGCGTGGCGAGCTATGGAAAAATCGCAATTGTCGATAGCCATG
TTAGTGACGCGCCTCGGCGTGCTCCTTTGGTGATTCGGCGACTGGTTACAGGAG
AGTAGGCAGTGAGCTATGGGCAAACCTCTGCAGTATTACTCAGAGGGAATGTG
CAATTGAGACTTGACGAGCGTCTCTTTGAGATGTGGCGCATGCTCTTGGCATTA
CCATAGTGAGCTTCCAGGTTGGGAAACCTGGACTGGGCCTATACTACCTGATA
GGGTCGCGGCTGGCCGCCTGTAACTAGTATAGTCAGTTGAAACCCCCATGGA
ATCTACTACTACTCTTTCATTTGCAACTGGATCCCTAAGAAACAGAGAGCCCG
TGTGTACCTTACCACCAGTGTAACACACGAGAAATCAAGTGGACCCTACACAT
ATGTAGTGTCTGACATGATCATGAAAGAAAACAGTAGAACCTCCCTTGCTATG
GCTTTCGTAGAAGGGAAGACACTTGTGTTCAACACCGGCACACAATTGGGACA
AGTTCATTCAGCTAACACAGGCAATAAACCTCAAGGAGCATACAACCATGGCT
CCGGTAGTATTACACAAATAAACTACTATGGTTCTGATTACTCCCAAGCATGG
AATCCTACACAACAGCAAATGGACCCCTCCCAGTTCACCAAACCAGTGACTGA
AATAGCCAATGCAATGGCAGGACCATCTCTCAAGGCACCTGACAAGGAAGAA
GAAGGGTACAGTGATAGGTTAATGCAATTGACAGCAGGAAACTCCTGTATAAC
AACACAAGAAGCAGCTAAAGCAGTTGTAGCATATGGACAATGGCCAAGTTAT
AACATAGATGCAGGAGAACATCTAGATCTTGCTACAACTCCAGGGACAGCAGT
GGACAGGTTTTACACCTTTGACAGCTTAAGATGGACCGACACACAAGTCGGTG
AATGGTCTCTGCCACTGCCTGGTGGTTTGATGGACACAGGCGTGTTTGGTCAAA
ACCTAAGATTCCACTACCTCTCCAGGATGGGCTTTTGTGTACATGTACAGTGCA
ATGCATCAAAATTCCACCAGGGTGCACTCATAGTTGCAATGATACCAGAGCAT
CAAACACCTACCCAAGTGAGTAACGGGTTTGAGTATAGAAATGGAGTGACCTA
CCAGGGAAACAATTATCCAACTGAACAACTACCTATATTCCACACCAGATTA
TAAACCTGAGGACCAACAACTCTGCAACAATAGTCTATCCATATACCAATTGT
ACTCCAGCAGGATTTGGTTTAGCACACAACTTTGTCACCCTGGTTATTAGGGTT
TTAGTGCCACTCAAGTACAATACAGGTGCTTCAACTTTTGTTCCTATTACTGTT
AGTGTGGCCCCAATGTGTTCACAGTTTGCAGGATTGAGATCAGCAGTAACAAG
ACAGGGTTTTCCTGTTAGGCAGGTACCAGGCAGCCAACAATTTATGACAACAC
AAAGAGATAGTGGGATACCAATCTACCCAGAGTTTCAGAAAACCCATAATTTC
AAATTGCCCGGAAGGGTAACCAATTTGCTACAAGTTGCTCAGGTGGGGACCTT
TCTCAAATTTAGTAATTCTACAAACGACACCAATAGAATCTATTTGAATTTGGA
TATTACACAGGGTGACCAGTCATCAAGGATGGTGGCTATTGATGTTAGCATGG
TTTCAGCCCACTTGTCCACCACATACCTTTCACGGTTGGCACAGATGTATGCCA
ATTACAGGGGTTCTGTTGTTTTTGAGTTTATGTTTTGTGGTAGCCAGATGGCCA
CTGGGAAACTACTGATAGCATACACACCTCCTGGTGGCACTTCCCCCACAACT
AGGACTGATGCAATGTTGGCAACACATGTTATTTGGGATATAGGTTTACAGTC
CACATGTAAAATGGTGGTCCCTTACATATCATCATCACAGTACAGACAGAACA
ATTTGACCCAAACAACACTATCTTACAATGGGTGGGTGACCATATTTCAACAG
ACGGCACTAGTTGTACCCCCTGGAGCCCCATCGACTTGCCAGTTAGTTGCCACC
GTGAGTGCAGCAGATAACTTTGTTCTTAGGATTCCCACAGATACCACATATTTT
GCTGATTATCAGGGTGATGTAAAAGATGTTGTACAGGCAAGCATAAATACCAC

*FIG. 2A*

CTTGCAAAATGCACTGAACACGAGACCACAGCAGGAACAGTCATCAAATGGT
ATAATGGTTAATCAAGGGGACGCACCTGCATTAACAGCGGCTGAGACTGGTGA
GTCTGATACTAATTCTGGTGGATCAACAATGGAACTTCAAGCAACAAACTGTG
TGTTTAGCCTAAGAGAAACAGATTTAGAGTACCTAATGTCTAGATATTCACTTA
TGTTTGAGGGCACTTTGGATTACACTGATGGGGCTGGCAAAAGGCATTTGAGG
TATGATTTGAATTTTAGACAAATTGGCAAATCAGGTAGTGATATTACCAAATTT
AAGGCTTTTACATACTGGAGGTTTGATTTAGATGCTGTGGTAATGATACTGGAG
GACAAGCCCGCAGCAGTGAGGAACCTTATGTTTCAGATTTTGTTTACCCCCCAT
GGGGGTGCTATACCTGGTACATATAACTCCCAGATTTGGAATGCTCCTAATTCA
ACCAGTATTTACACCAGAGTAGGAAATTGTCCTGCCTCGTTTAGGATACCTTTT
ATGTCTGTTTGCAATTATTATACTTCCTTTTATGATGGTGATGGGAATTTTGATA
TGAATGGTGCGTCTTATGGTATTAATCCAGGTGATTTTATAGGCACAATATCTA
TTAGGATGGCCAATGACTTTTTTTTACTAATACTACCACTGGTTCCTTTAGAG
CTAAGATCTTTCTTAGGCCTGTAAATATTGAAGCCTATATGCCTAGACCTCTTA
TTTCCTACAAGGCTAATGGTGATGCCAGACAAGATAGTTCACAATACTACCCT
GCAGCCCAGACGGGGTTTTACCCCGCGGAACAGCTGGGACCCTATGAAATTTG
CCAAACCAGACATGCTTCAGAGCTAATTGATACTAAATGGGCAAGATACTCTT
GCTCGGTTAAATTTGACAGAGGTTCATTTACAGCATGGTTTGTGGGAGAAGAC
CTGCTTTTGGTACCCTACCATGCTGCAAACAATTGGAGTCAGACAACACATGT
GTTCCTGTGGAGAGCATGGGATAAGGACTGGAGAGACCATCCTGAATTGGAAA
TGAAGATCCCCATTTTGGACATGTGGACTGATTCTACCAGAGATGTCACTTTTC
TTAAATTGGCCTACGCTACACCATACTGGTTGGAGATGCCAGCAAAAGGTTCT
GCCATAGGTGATTACATTGTAGTTGTGAATTCAGCCCACTTCCCATGGAAACA
GTACTCAGGCCCAAAACCATTTAGACACCCTACTTACATATTGGACAACATA
CCCAATACAGACTGTGGATGCATGCTGGTGATGCTGACAATGGCTTCTGTGGA
GCCGGTTTAATATCTAGAGGTAAACTTTATGGTATAGTTACAGCAAGGACAGA
GGCTAAATCAGGTGGTACCTATGTGGCCTACACTGAACTGGATGAAGATACCT
TCCTACAAACACAACAAAGATGTTTTGATTTTGGAATGGATTCACACTTCAATC
TTGGAATGCATGACTGGGTCCAGGGACTCGGCCAGGTGTTCGGAGAGGGTGTT
TCTGGGGAGGTGAAAAGACAAGTGGAAGATTACTTAGGCCAGATCAAGCCCA
TTATTGATTCAGGTACCAATAAAATTAAGGATGTTATTAAAGATGAAATGGTT
AGTGCCAGTATGTCCTTGTTAGTTAAGGTAGTTGCTTCCCTAGTACTGTATATG
AATTCTAAGGATGACTGTAAAATGTCCACTTTAGCTTCATTGGGTGCCCTTTTA
GGTGTAGATATATTTTTGACTGATCCTATTATGTACCTGTATAGTAAGATGACT
GGAGAACCTCACAGACAGGGGCCAACAGAGTGGCTTAAAGAGTTCAATACAG
CCATAAATGCATTTAAAGGATTTGATTTTCTCTGCTCCAAATTAATGCAATTGA
TTGAATGGATTAAACAGTTTTTCCAGA GGGTTGAACCAGAGTACAAGGAGTTT
AAGGAGTTACTTGAATCTTGGCCCAAAGTTTGTGCCAAAGTGTTGGAGTTTAA
GAACTGCAAAACAACACTAGGACAAGA AGATATTTGTCAAATAAAGGTTTACA
TAGACAAAATGATTGAGTTGGGAAACAAATATGGCCACAAATTTCATTTACAG
ATGTCTCAGTTACTGCAATGTTCAAACATAATAAACAAAGCTTACAGTAACAT
GACAAGATCTAGACATGAACCTGTTGCAATTCTTATACATGGTGCTCCTGGAA
CTGGAAAGTCACTTGCTACAGAAATAATTGGTAGGGCAATAGCAGATAAGTTA
GATAATCAGAGACCTTACACACTCCCACCAGACCCCAAACATTTTGATGGATA
TAATCAACAGAAAGTGGTTATTATGGATGATTAGGACAAAACCCAGATGGTG
AAGATTGCAAGATGTTTTGCCAGATGGTGTCAACCACTACTTACATTCCACCTA
TGGCCTCCTTAGATGAGAAAGGACTTCCCTTTATTTCTGACTTTGTTCTTGCTTC
TACTAACCAGCATGCTTTGACCCCCAGAACTATTGCTGAGCCTGATGCTATTAA

FIG. 2B

```
TAGAAGATGGTTTATGAATGTAGATATTCACCTTAAGAAAGAATACAAGGATG
ATAGAGGAAGGTTAGACATGTCAAAGTGTTTGCCTTGTAAAGATTGCAAACCA
GTGAATTTCAGGAGATGTAACCCATTGATTTGTGGAAAAGCCATCATTTTACTG
GACAGGAAAACCCAGAAAAACTGGACCCTTGATTCAGCAGTTAGTTACTTATT
GGATGAATCAGAGAGAAGAAAAGGGTTCTTAAATGTAGTGGATGCAATCTTTC
AGGGACCTGTGCAGATTCCAGAATGTGTTAGAGAGGATGAACTGAAGAGGAA
GAAGGTGAATTCAGAGAGAGACATCCAAGCTGATGTGATGGAATTAGTTAGAT
GTACAAAATCCCCTGTTATAATTGAGGAATTAGAGAAAGCAGGTTTCATCATT
CCTGTTGAGGCAGAAGTGATTAGACAGACTAGTAATGTGAATAATGTAACCCA
AATTATTTCAGCAACTCTAGCTAGTTTGGCAGCTATAATTTCTGTAGGGACTGT
AGTTTATTTAATGGTTAAGTTGTTTTCCACAAAACAAGGAGCATACACTGGTGT
GCCCAAACCAGAAACCAAGAGACCTGTACTTAGAAAAGCAGTAGTGCAGGGC
CCAGACATGGAATTTGCCAAGTCAATTATGAGATCAAATCTGTGTCAGGTAAC
CACCAGTGTGGGACCCTTTACCGGGCTGGGCATCTGTGATAACATCTTGGTGCT
ACCACGACATGCTTATGTGAGTGGAAACATAGTGTTAGATGGTATAGACATTC
CTGTAACAGATGCTGTAGAATTAGAAGCAGAGGAGGGAAATTTGGAATTAGTA
CAGTTAACCCTTAAGAGAAATGAAAAATTTAGGGATATTAGAAAGTTTTTAAG
TAATGGTTTTCACAGTGAGAATGATTGCTGGTTGTGCATTAATTCTGAGATGTT
TTCTAATGTATATATACCTCTTAAGAGTGTTTCTGCCTTTGGATTCCTTAACCTT
TCTATGACTCCTACTTACAGAACACTTGTTTACAATTACCCTACCAAGATGGGA
CAATGTGGTGGTGTTGTGCTGAAAGCAGGAAAGATTTTAGGCATACATATTGG
TGGTGATGGAACCAGAGGGTTTGCAGCCCTACTGAAGAGAGATTACTTTGTAA
ACAAACAAGGTTTGATAACAGAGAGATACACACCATCAAAACCTATTAATGTT
AGAACAAAGACAGCTTTCCAACCTTCTGTTTTTCATGATGTCTTTCCTGGGAGT
AAGGAACCTGCAGCAATGAGTGTGCATGATCCAAGACTTGAAGTGGATCTGGA
AGAAGCAATATTTGCAAAGTACAAAGGCAATGTTGACACCACACTTCCAGAAG
AAGCACTTATAGCAATTGACCATTTGGTTTCCAAATTTAAGGCAATTGTACCAG
ACAATCTGTGTGAGAAGATGTCATTGGAGGATGTTGTCTATGGTACTGATAATC
TGGATGGACTAGATTTAACCACTTCAGCAGGTTACCCCTACAACACCTTGGGG
ATTAGAAAGAAAGATCTTATTCCTCCCAAAGGACAGTCTCTTTCCCCTCTTATA
AAGGCTCTTGATCTTTATGGATATGATTTACCCTTTACTACTTACATGAAGGAT
GAGTTGAGACCAAAGGAGAAAGTGAAGATGGGCAAAACCAGGGTCATTGAGT
GTTCATCACTTAATGATACCATAATGATGAAGCAGACTTTTGGTCATCTGTTCC
AGACATGCCACAAGAATCCTGGAACCTACACTGGTGTAGCTGTAGGCTGCAAC
CCAGATGTGGATTGGTCAAAGTTTGCTGCTGAGATTGGTGATGCCTATGTGTGT
GCTTTTGATTATACAAATTGGGATGCTAGTCTGTCACCTTTGTGGTTTGATGCTT
TAAAGTTGTTTCTTTCCAAACTAGGTTACAGTGGTAGGGATTTAGTTTTGATTG
ATCAGTTGTGTTATTCAAATCACATTTACAAGAATAAGGGATACAAAGTTACC
GGCGGTATGCCATCTGGTTGCTCCGGAACTAGTATCTTTAATAGCATTATTAAC
AATATAGTTATTAGGACTTTAATAATGTTAGCATATAAGAATATTAATTTAGAT
GAGTTGTTAGTTTTATGTTATGGTGATGATTTATTGGTTGCCTATCCCTATGAAT
TAGATCCAAATGTGCTGGTTCCATTGGCAAAGAGTTATGGTTTGACCATAACA
CCAGCAGACAAATCAACAACTTTCCAAACAGGAACAAAGTTAACAGATGTTAC
CTTCCTGAAGAGGGGTTTCAAATTCGATGAGGAATACCCCTTCCTGTGTCATCC
TGTATTTCCTATGGAGGAGGTGCATGAATCAATTAGATGGACCAAGAATGCCA
GCTATACCCAGGAACATGTTACATCGCTGTGTCTTTTGGCATGGCACAATGGTG
AGGAGGTTTATGAAGAGTTCTGTACGAAAATCAGATCAGTTCCAGTAGGCAGA
GCTCTCATATTACCACCTTACTCTCAGCTGCGTAGGTCTTGGTTAGATATGTTTT
AGGCGGCGTGAACATATCAGTGATACAGGATTAACAATTAGGCTAATTGGCAA
TAGACCCTAAGCCGCCTATAGGGTCTACAA
```

*FIG. 2C*

ATTENUATED PORCINE SAPELOVIRUS STRAIN AND IMMUNOGENIC COMPOSITIONS THEREFROM

CROSS-REFERENCE TO RELATED APPLICATIONS

This application claims priority under 35 U.S.C. § 119 to provisional application Ser. No. 62/774,511, filed Dec. 3, 2018, herein incorporated by reference in its entirety.

SEQUENCE LISTING

The instant application contains a Sequence Listing which has been submitted in ASCII format via EFS-Web and is hereby incorporated by reference in its entirety. Said ASCII copy, created on Feb. 8, 2020, is named CHEN_P12766_seq_ST25.txt and is 20,480 bytes in size.

FIELD OF THE INVENTION

The present invention is directed to novel immunogenic compositions that protect swine from disease caused by porcine *Sapelovirus* (PSV).

BACKGROUND OF THE INVENTION

Porcine *Sapelovirus* (PSV) is characterized by a wide range of symptoms, including diarrhea, skin lesions, myelitis, polioencephalomyelitis with ataxia and eventual limb paralysis, reproductive failure (SMEDI syndrome), atypical neurologic disease and has a common mortality rate of 1-3% and occasionally up to 10 on affected farms. The causative agent, porcine *Sapelovirus* (PSV), is a single stranded, positive sense polyadenylated and nonenveloped RNA virus belonging to the *Sapelovirus* genus of the family Picornaviridae. PSV has a total genome size of approximately 7.5 kb to 8.3 kb and contains 1 open reading frame encoding four structural proteins (VP1, VP2, VP3, and VP4) and seven nonstructural proteins (2A, 2B, 2C, 3A, 3B, 3C, and 3D). The *Sapelovirus* genus is closely related to the genus *Enterovirus* and includes three known species, *Avian Sapelovirus*, *Sapelovirus* A (porcine *Sapelovirus*), and *Sapelovirus* B (simian *Sapelovirus*), with a single serotype. There is currently no commercially available vaccine or immunization for PSV, and little is known about cross-protection between strains.

Incidence of PSV increased dramatically in 2017. It has been isolated in many countries around the world, including the United States of America, China, Japan, India, South Korea, Brazil, Germany, the United Kingdom, and Spain. Current treatments include isolating herd specific strains and then generating herd custom vaccines to use against an already infected population of animals.

PSV generally ruptures cells in culture, and there is a need to identify strains that are appropriate for the culturing of sufficient virus for commercial vaccine preparation. Additionally, there is a need to develop vaccines that provide effective cross protection against known isolates of PSV, and which are expected to provide effective cross protection against evolving PSV strains worldwide.

SUMMARY OF THE INVENTION

The present invention encompasses immunogenic compositions comprising variant PSV strains passaged from prototype strains. The prototype strains were isolated from the brain or spinal cords of swine showing front limp ataxia, without gross lesions in the spinal cords, muscles, or bone of the spinal columns, and showing nonsuppurative myelitis in spinal cord as histological lesions. They were then serial passaged to create a culture stable variant strain. The U.S. PSV variant strain US/ISU26908B/18 is genetically different in the polyprotein open reading frame (ORF) from the sample isolated strain by a 3-nt insertion at position 3,006, and several single nucleotide polymorphs (SNPs) at positions 1,318, 2,360, 2,793, 4,154, and 6,115.

Thus, the invention comprises an immunogenic composition, suitable to be used as a vaccine, which comprises a variant PSV strain of the invention, preferably live and attenuated, or an immunogenic fragment thereof, one or more adjuvants, and optionally one or more excipients, in an amount effective to elicit production of neutralizing antibodies in swine. The adjuvant preferably provides an oil-in-water emulsion with additional components. The immunogenic compositions of the invention protect swine from infection by PSV, and are effective in single doses, in two-dose programs, or in vaccination programs involving multiple doses, which may be spread apart by at least a week, and optionally at greater intervals of time, such as one to several months. It should be noted that depending on the level of epidemic threat in a particular swine population, the vaccine dose program of one, two, or multiple doses may be repeated, from time to time, as a precautionary measure. Additionally, it should be noted that vaccinating a mother sow during pregnancy will provide protection to a young piglet, via maternal transfer of antibodies and T-cells in colostrum and milk, although such protection may need to be followed up with additional vaccination doses to the piglet. Vaccination of all swine, including piglets and adults is contemplated.

The present invention includes novel nucleotide and amino acid sequences of PSV, including novel genotypes thereof, all of which are useful in the preparation of vaccines for treating and preventing diseases in swine and other animals. Vaccines provided according to the practice of the invention are effective against multiple swine PSV genotypes and isolates. Diagnostic and therapeutic polyclonal and monoclonal antibodies are also a feature of the present invention, as are infectious clones useful in the propagation of the virus and in the preparation of vaccines. Of particular importance, there are disclosed vaccines that comprise, as antigen, a whole virus (live or attenuated) or a single antigenic protein of a PSV open reading frame, most particularly from the first 2.7 kb of the ORF, more particularly the region encoding the structural genes, and also fragments of the full-length sequence encoding the PSV proteins. The invention also provides the full-length genomic sequences of PSV strains at different passages in cell culture that can replicate efficiently in host animals and tissue culture.

The present invention provides a method of treating or preventing a disease or disorder in an animal caused by infection with PSV, including disease states that are directly caused by PSV, and disease states contributed to or potentiated by PSV. Disease states in swine that may be potentiated by PSV, and which may also be treated or prevented according to the practice of the invention, include those caused by or associated with *Enterovirus*.

The present invention also includes the option to administer a combination vaccine, that is, a bivalent or multivalent combination of antigens, which may include live, modified live, or inactivated antigens against the non-PSV pathogen, with appropriate choice of adjuvant.

Based in part upon the unique PSV sequences as disclosed herein, the present invention also provides a diagnostic kit for differentiating between porcine animals vaccinated with the above described PSV vaccines and porcine animals infected with field strains of PSV.

Representative embodiments of the invention include an isolated polynucleotide sequence that includes a genomic polynucleotide which encodes variant PSV proteins which are attenuated and may be used as an immunogenic composition. This can include whole genome sequences selected from the group consisting of:

(a) SEQ ID NOS 1 or 2 or an immunogenic fragment thereof that encodes the PSV virus variants;

(b) the complement of any sequence in (a);

(c) a polynucleotide that hybridizes with a sequence of (a) or (b) under stringent conditions defined as hybridizing to filter bound DNA in 0.5M NaHPO4, 7% SDS, 1 mM EDTA at 65° C., and washing in 0.1×SSC/0.1% SDS at 68° C.

(d) a polynucleotide that is at least 70% identical to the polynucleotide of (a) or (b);

(e) a polynucleotide that is at least 80% identical to the polynucleotide of (a) or (b);

(f) a polynucleotide that is at least 90% identical to the polynucleotide of (a) or (b); and (g) a polynucleotide that is at least 95% identical to the polynucleotide of (a) or (b)

Preferably in combination with a second heterologous sequence.

The invention further provides RNA and DNA molecules, their complements, fragments and vectors and plasmids for the expression of any such RNA or DNA polynucleotides, and for PSV virus that is expressed from such nucleotide sequences, wherein said virus is live, or fully or partially attenuated.

The invention also provides a vaccine that comprises a polynucleotide sequence as aforementioned, and corresponding nucleotide sequences that may function as infectious clones.

The invention further provides nucleic acid sequences and resultant protein variants that have amino acid substitutions, and which reduce virulence, cause attenuation and allow the compositions to be used safely as immunogenic compositions and as vaccines.

In a further embodiment the invention includes vaccine compositions comprising a live attenuated variant strain PSV, and a carrier, wherein said composition is capable of protecting swine from challenge by both variant and prototype strains of PSV and preventing or treating one or more of symptoms associated with PSV infection, and wherein achievement of protection is determined by an endpoint selected from the group consisting of prevention or control of any of the PSV infection symptoms of diarrhea, skin lesions, myelitis, polioencephalomyelitis with ataxia and eventual limb paralysis, reproductive failure (SMEDI syndrome), atypical neurologic disease, and mortality.

The invention further includes passages and amino acid substitution from passaging the prototype virus.

In a further embodiment the invention includes vaccine compositions comprising a live attenuated variant strain PSV, and a carrier, wherein said composition is capable of protecting swine from challenge by both variant and prototype strains of PSV and preventing or treating one or more of symptoms associated with PSV infection, and wherein achievement of protection is determined by an endpoint selected from the group consisting of prevention or control of any of the PSV infection symptoms, wherein said strain encodes proteins with a substitution of proteins encoded by SEQ ID NO: 2 and their conservative variants and proteins with the specific substitutions and 99% homology to the remainder of the sequences.

It is within the scope of the invention to make additional modifications in any PSV passages described herein, wherein said modifications include introducing mutations of another passage described herein using known methods according to one of skill in the art, for example, homologous recombination.

GenBank® is the recognized United States-NIH genetic sequence database, comprising an annotated collection of publicly available DNA sequences, and which further incorporates submissions from the European Molecular Biology Laboratory (EMBL) and the DNA DataBank of Japan (DDBJ), see Nucleic Acids Research, January 2013, v 41(D1) D36-42 for discussion.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIGS. 1A-C show the sequence of the strain of the invention (SEQ ID NO: 1).

FIGS. 2A-C show the whole genome sequence of the passaged PSV cell culture isolate US/ISU26908B/18 passage 7, on ST cells (SEQ ID NO: 2).

DETAILED DESCRIPTION OF THE INVENTION

The following definitions and introductory matters are applicable in the specification.

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

The term "adjuvant" refers to a compound that enhances the effectiveness of the vaccine and may be added to the formulation that includes the immunizing agent. Adjuvants provide enhanced immune response even after administration of only a single dose of the vaccine. Adjuvants may include, for example, muramyl dipeptides, pyridine, aluminum hydroxide, dimethyldioctadecyl ammonium bromide (DDA), oils, oil-in-water emulsions, saponins, cytokines, and other substances known in the art. Examples of suitable adjuvants are described in U.S. Patent Application Publication No. US2004/0213817 A1. "Adjuvanted" refers to a composition that incorporates or is combined with an adjuvant.

"Antibodies" refers to polyclonal and monoclonal antibodies, chimeric, and single chain antibodies, as well as Fab fragments, including the products of a Fab or other immunoglobulin expression library. With respect to antibodies, the term, "immunologically specific" refers to antibodies that bind to one or more epitopes of a protein of interest, but which do not substantially recognize and bind other molecules in a sample containing a mixed population of antigenic biological molecules.

An "attenuated" PSV as used herein refers to a PSV which is capable of infecting and/or replicating in a susceptible host but is non-pathogenic or less-pathogenic to the susceptible host. For example, the attenuated virus may cause no observable/detectable clinical manifestations, or less clinical manifestations, or less severe clinical manifestations, or exhibit a reduction in virus replication efficiency and/or infectivity, as compared with the related field isolated strains. The clinical manifestations of PSV infection can include, without limitation, clinical diarrhea, vomiting, lethargy, loss of condition and dehydration.

An "epitope" is an antigenic determinant that is immunologically active in the sense that once administered to the host, it is able to evoke an immune response of the humoral (B cells) and/or cellular type (T cells). These are particular chemical groups or peptide sequences on a molecule that are antigenic. An antibody specifically binds a particular antigenic epitope on a polypeptide. In the animal most antigens will present several or even many antigenic determinants simultaneously. Such a polypeptide may also be qualified as an immunogenic polypeptide and the epitope may be identified as described further.

The term "immunogenic fragment" as used herein refers to a polypeptide or a fragment of a polypeptide, or a nucleotide sequence encoding the same which comprises an allele-specific motif, an epitope or other sequence such that the polypeptide or the fragment will bind a major histocompatibility complex (MHC) molecule and induce a cytotoxic T lymphocyte ("CTL") response, and/or a B cell response (for example, antibody production), and/or T-helper lymphocyte response, and/or a delayed type hypersensitivity (DTH) response against the antigen from which the immunogenic polypeptide or the immunogenic fragment is derived. A DTH response is an immune reaction in which T cell-dependent macrophage activation and inflammation cause tissue injury. A DTH reaction to the subcutaneous injection of antigen is often used as an assay for cell-mediated immunity.

With the term "induction of an immunoprotective response" is meant a (humoral and/or cellular) immune response that reduces or eliminates one or more of the symptoms of disease, i.e. clinical signs, lesions, bacterial excretion and bacterial replication in tissues in the infected subject compared to a healthy control. Preferably said reduction in symptoms is statistically significant when compared to a control.

An "infectious DNA molecule", for purposes of the present invention, is a DNA molecule that encodes the necessary elements for viral replication, transcription, and translation into a functional virion in a suitable host cell.

The term "isolated" is used to indicate that a cell, peptide or nucleic acid is separated from its native environment. Isolated peptides and nucleic acids may be substantially pure, i.e. essentially free of other substances with which they may bound in nature.

For purposes of the present invention, the nucleotide sequence of a second polynucleotide molecule (either RNA or DNA) is "homologous" to the nucleotide sequence of a first polynucleotide molecule, or has "identity" to said first polynucleotide molecule, where the nucleotide sequence of the second polynucleotide molecule encodes the same polyaminoacid as the nucleotide sequence of the first polynucleotide molecule as based on the degeneracy of the genetic code, or when it encodes a polyaminoacid that is sufficiently similar to the polyaminoacid encoded by the nucleotide sequence of the first polynucleotide molecule so as to be useful in practicing the present invention. Homologous polynucleotide sequences also refers to sense and anti-sense strands, and in all cases to the complement of any such strands. For purposes of the present invention, a polynucleotide molecule is useful in practicing the present invention, and is therefore homologous or has identity, where it can be used as a diagnostic probe to detect the presence of PSV or viral polynucleotide in a fluid or tissue sample of an infected pig, e.g. by standard hybridization or amplification techniques. Generally, the nucleotide sequence of a second polynucleotide molecule is homologous to the nucleotide sequence of a first polynucleotide molecule if it has at least about 70% nucleotide sequence identity to the nucleotide sequence of the first polynucleotide molecule as based on the BLASTN algorithm (National Center for Biotechnology Information, otherwise known as NCBI, (Bethesda, Md., USA) of the United States National Institute of Health). In a specific example for calculations according to the practice of the present invention, reference is made to BLASTP 2.2.6 [Tatusova T A and T L Madden, "BLAST 2 sequences—a new tool for comparing protein and nucleotide sequences." (1999) FEMS Microbiol Lett. 174:247-2501 Briefly, two amino acid sequences are aligned to optimize the alignment scores using a gap opening penalty of 10, a gap extension penalty of 0.1, and the "blosum62" scoring matrix of Henikoff and Henikoff (Proc. Nat. Acad. Sci. USA 325 89:10915-10919. 1992). The percent identity is then calculated as: Total number of identical matches×100/divided by the length of the longer sequence+number of gaps introduced into the longer sequence to align the two sequences.

Preferably, a homologous nucleotide sequence has at least about 75% nucleotide sequence identity, even more preferably at least about 80%, 85%, 90% and 95% nucleotide sequence identity. Since the genetic code is degenerate, a homologous nucleotide sequence can include any number of "silent" base changes, i.e. nucleotide substitutions that nonetheless encode the same amino acid.

A homologous nucleotide sequence can further contain non-silent mutations, i.e. base substitutions, deletions, or additions resulting in amino acid differences in the encoded polyaminoacid, so long as the sequence remains at least about 70% identical to the polyaminoacid encoded by the first nucleotide sequence or otherwise is useful for practicing the present invention. In this regard, certain conservative amino acid substitutions may be made which are generally recognized not to inactivate overall protein function: such as in regard of positively charged amino acids (and vice versa), lysine, arginine and histidine; in regard of negatively charged amino acids (and vice versa), aspartic acid and glutamic acid; and in regard of certain groups of neutrally charged amino acids (and in all cases, also vice versa), (1) alanine and serine, (2) asparagine, glutamine, and histidine, (3) cysteine and serine, (4)glycine and proline, (5) isoleucine, leucine and valine, (6) methionine, leucine and isoleucine, (7)phenylalanine, methionine, leucine, and tyrosine, (8) serine and threonine, (9) tryptophan and tyrosine, (10) and for example tyrosine, tyrptophan and phenylalanine. Amino acids can be classified according to physical properties and contribution to secondary and tertiary protein structure. A conservative substitution is thus recognized in the art as a substitution of one amino acid for another amino acid that has similar properties, and exemplary conservative substitutions may be found in WO 97/09433, page 10, published Mar. 13, 1997 (PCT/GB96/02197, filed Sep. 6, 1996. Alternatively, conservative amino acids can be grouped as described in Lehninger, (Biochemistry, Second Edition; Worth Publishers, Inc. N.Y.: N.Y. (1975), pp. 71-77). Protein sequences can be aligned using both Vector NTI Advance 11.5 and CLUSTAL 2.1 multiple sequence alignment. As used herein the recitation of a particular amino acid or nucleotide sequence shall include all silent mutations with respect to nucleic acid sequence and any and all conservatively modified variants with respect to amino acid sequences.

Homologous nucleotide sequences can be determined by comparison of nucleotide sequences, for example by using BLASTN, above. Alternatively, homologous nucleotide sequences can be determined by hybridization under selected conditions. For example, the nucleotide sequence of a second polynucleotide molecule is homologous to SEQ ID NO:1 (or any other particular polynucleotide sequence) if it hybridizes to the complement of SEQ ID NO:1 under moderately stringent conditions, e.g., hybridization to filter-bound DNA in 0.5 M $NaHPO_4$, 7% sodium dodecyl sulfate (SDS), 1 mM EDTA at 65° C., and washing in 0.2×SSC/0.1% SDS at 42° C. (see Ausubel et al editors, Protocols in Molecular Biology, Wiley and Sons, 1994, pp. 6.0.3 to 6.4.10), or conditions which will otherwise result in hybridization of sequences that encode a PSV virus as defined below. Modifications in hybridization conditions can be empirically determined or precisely calculated based on the length and percentage of guanosine/cytosine (GC) base pairing of the probe. The hybridization conditions can be calculated as described in Sambrook, et al., (Eds.), Molecular Cloning: A Laboratory Manual, Cold Spring Harbor Laboratory Press: Cold Spring Harbor, N.Y. (1989), pp. 9.47 to 9.51.

In another embodiment, a second nucleotide sequence is homologous to SEQ ID NO: 1 (or any other sequence of the invention) if it hybridizes to the complement of SEQ ID NO: 1 under highly stringent conditions, e.g. hybridization to filter-bound DNA in 0.5 M $NaHPO_4$, 7% SDS, 1 mM EDTA at 65° C., and washing in 0.1×SSC/0.1% SDS at 68° C., as is known in the art.

It is furthermore to be understood that the isolated polynucleotide molecules and the isolated RNA molecules of the present invention include both synthetic molecules and molecules obtained through recombinant techniques, such as by in vitro cloning and transcription.

It should be noted that many of the vaccine-capable attenuated PSV viruses of the present invention contain substantial deletions of ORF3 protein, resulting from attenuating mutations in the ORF3 nucleotide sequence, that cause substantial internal deletions and/or most typically the appearance of truncated translation resultant from frameshifting and the appearance of stop codons. It should therefore be noted that within the practice of the present invention, alignment and percent identity calculations and stated identity results (whether or nucleotide or amino acid sequences) can be calculated with or without reference to deleted ORF3 sequences.

"Mammals" include any warm-blooded vertebrates of the Mammalia class, including humans.

A "pharmaceutically acceptable carrier" means any conventional pharmaceutically acceptable carrier, vehicle, or excipient that is used in the art for production and administration of vaccines. Pharmaceutically acceptable carriers are typically non-toxic, inert, solid or liquid carriers.

The terms "porcine" and "swine" are used interchangeably herein and refer to any animal that is a member of the family Suidae such as, for example, a pig.

A "susceptible" host as used herein refers to a cell or an animal that can be infected by PSV. When introduced to a susceptible animal, an attenuated PSV may also induce an immunological response against the PSV or its antigen, and thereby render the animal immunity against PSV infection.

The term "vaccine" refers to an antigenic preparation used to produce immunity to a disease, in order to prevent or ameliorate the effects of infection. Vaccines are typically prepared using a combination of an immunologically effective amount of an immunogen together with an adjuvant effective for enhancing the immune response of the vaccinated subject against the immunogen.

Vaccine formulations will contain a "therapeutically effective amount" of the active ingredient, that is, an amount capable of eliciting an induction of an immunoprotective response in a subject to which the composition is administered. In the treatment and prevention of PSV disease, for example, a "therapeutically effective amount" would preferably be an amount that enhances resistance of the vaccinated subject to new infection and/or reduces the clinical severity of the disease. Such protection will be demonstrated by either a reduction or lack of symptoms normally displayed by a subject infected with PSV, a quicker recovery time and/or a lowered count of virus particles. Vaccines can be administered prior to infection, as a preventative measure against PSV. Alternatively, vaccines can be administered after the subject already has contracted a disease. Vaccines given after exposure to PSV may be able to attenuate the disease, triggering a superior immune response than the natural infection itself.

For the purpose of the practice of all aspects of the invention, it is well known to those skilled in the art that there is no absolute immunological boundary in immunological assays in regard of animals that are seronegative for exposure to a particular antigen or pathogen, and those that are seropositive (having been exposed to a vaccine or pathogen). Nonetheless, those skilled in the art would recognize that in serum neutralization assays, seropositive animals would generally be detected at least up to a 1:1000 serum dilution, whereas a seronegative animal would be expected not to neutralize at a higher dilution that about 1:20 or 1:10.

Vaccine Formulations/Immunogenic Compositions

The invention also relates to an immunogenic composition, suitable to be used as a vaccine, which comprises a variant PSV strain according to the invention. The immunogenic compositions according to the invention elicit a specific humoral immune response toward the PSV comprising neutralizing antibodies.

The preferred immunogenic compositions based upon the variant strains disclosed herein can provide live, attenuated viruses which exhibit high immunogenicity while at the same time not producing dangerous pathogenic or lethal effects.

The immunogenic compositions of this invention are not, however, restricted to any particular type or method of preparation. These include, but are not limited to, infectious DNA vaccines (i.e., using plasmids, vectors or other conventional carriers to directly inject DNA into pigs), live vaccines, modified live vaccines, inactivated vaccines, subunit vaccines, attenuated vaccines, genetically engineered vaccines, etc. These vaccines are prepared by standard methods known in the art.

The present invention preferably includes vaccine compositions comprising a live, attenuated variant PSV of the invention and a pharmaceutically acceptable carrier. As used herein, the expression "live, attenuated PSV of the invention" encompasses any live, attenuated PSV strain that includes one or more of the variations described herein. The pharmaceutically acceptable carrier can be, e.g., water, a stabilizer, a preservative, culture medium, or a buffer. Vaccine formulations comprising the attenuated PSV of the invention can be prepared in the form of a suspension or in a lyophilized form or, alternatively, in a frozen form. If frozen, glycerol or other similar agents may be added to enhance stability when frozen. The advantages of live attenuated vaccines, in general, include the presentation of all the relevant immunogenic determinants of an infectious agent in its natural form to the host's immune system, and the need for relatively small amounts of the immunizing agent due to the ability of the agent to multiply in the vaccinated host.

Attenuation of the virus for a live vaccine, so that it is insufficiently pathogenic to substantially harm the vaccinated target animal, may be accomplished by known procedures, including preferably by serial passaging. The following references provide various general methods for attenuation of coronaviruses, and are suitable for attenuation or further attenuation of any of the strains useful in the practice of the present invention: B. Neuman et al., Journal of Virology, vol. 79, No. 15, pp. 9665-9676, 2005; J. Netland et al., Virology, v 399(1), pp. 120-128, 2010; Y-P Huang et al., "Sequence changes of infectious bronchitis virus isolates in the 3' 7.3 kb of the genome after attenuating passage in embryonated eggs, *Avian* Pathology, v. 36 (1), (Abstract), 2007; and S. Hingley et al., Virology, v. 200(1) 1994, pp. 1-10; see U.S. Pat. No. 3,914,408; and Ortego et al., Virology, vol. 308 (1), pp. 13-22, 2003.

Additional genetically engineered vaccines, which are desirable in the present invention, are produced by techniques known in the art. Such techniques involve, but are not limited to, further manipulation of recombinant DNA, modification of or substitutions to the amino acid sequences of the recombinant proteins and the like.

Genetically engineered vaccines based on recombinant DNA technology are made, for instance, by identifying alternative portions of the viral gene encoding proteins responsible for inducing a stronger immune or protective response in pigs (e.g., proteins derived from VP1, VP2, VP3, VP4, etc.). Various subtypes or isolates of the viral protein genes can be subjected to the DNA-shuffling method. The resulting heterogeneous chimeric viral proteins can be used as broad protecting subunit vaccines. Alternatively, such chimeric viral genes or immuno-dominant fragments can be cloned into standard protein expression vectors, such as the baculovirus vector, and used to infect appropriate host cells (see, for example, O'Reilly et al., "Baculovirus Expression Vectors: A Lab Manual," Freeman & Co., 1992). The host cells are cultured, thus expressing the desired vaccine proteins, which can be purified to the desired extent and formulated into a suitable vaccine product.

If the clones retain any undesirable natural abilities of causing disease, it is also possible to pinpoint the nucleotide sequences in the viral genome responsible for any residual virulence, and genetically engineer the virus avirulent through, for example, site-directed mutagenesis. Site-directed mutagenesis is able to add, delete or change one or more nucleotides (see, for instance, Zoller et al., DNA 3:479-488, 1984). An oligonucleotide is synthesized containing the desired mutation and annealed to a portion of single stranded viral DNA. The hybrid molecule, which results from that procedure, is employed to transform bacteria. Then double-stranded DNA, which is isolated containing the appropriate mutation, is used to produce full-length DNA by ligation to a restriction fragment of the latter that is subsequently transfected into a suitable cell culture. Ligation of the genome into the suitable vector for transfer may be accomplished through any standard technique known to those of ordinary skill in the art. Transfection of the vector into host cells for the production of viral progeny may be done using any of the conventional methods such as calcium-phosphate or DEAE-dextran mediated transfection, electroporation, protoplast fusion and other well-known techniques (e.g., Sambrook et al., "Molecular Cloning: A Laboratory Manual," Cold Spring Harbor Laboratory Press, 1989). The cloned virus then exhibits the desired mutation. Alternatively, two oligonucleotides can be synthesized which contain the appropriate mutation. These may be annealed to form double-stranded DNA that can be inserted in the viral DNA to produce full-length DNA.

An immunologically effective amount of the vaccines of the present invention is administered to a pig in need of protection against viral infection. The immunologically effective amount or the immunogenic amount that inoculates the pig can be easily determined or readily titrated by routine testing. An effective amount is one in which a sufficient immunological response to the vaccine is attained to protect the pig exposed to the PSV virus. Preferably, the pig is protected to an extent in which one to all of the adverse physiological symptoms or effects of the viral disease are significantly reduced, ameliorated or totally prevented.

Vaccines of the present invention can be formulated following accepted convention to include acceptable carriers for animals, such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's Pharmaceutical Science, 18th ed., 1990, Mack Publishing, which is incorporated herein by reference.

Vaccines of the present invention may further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, ionic polysaccharides, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 µg/ml Quil A, 100 µg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 µg/ml Quil A, and 50 µg/ml cholesterol. Other immunomodulatory agents that can be included in the vaccine include, e.g., one or more interleukins, interferons, or other known cytokines.

Additional adjuvant systems permit for the combination of both T-helper and B-cell epitopes, resulting in one or more types of covalent T-B epitope linked structures, with may be additionally lipidated, such as those described in WO2006/084319, WO2004/014957, and WO2004/014956.

In a preferred embodiment of the present invention PSV proteins or fragments thereof, is formulated with 5% AMPHIGEN® as discussed hereinafter.

Adjuvant Components

The vaccine compositions of the invention may or may not include adjuvants. In particular, as based on an orally infective virus, the modified live vaccines of the invention may be used adjuvant free, with a sterile carrier. Adjuvants that may be used for oral administration include those based on CT-like immune modulators (rmLT, CT-B, i.e. recombinant-mutant heat labile toxin of *E. coli*, Cholera toxin-B subunit); or via encapsulation with polymers and alginates, or with mucoadhesives such as chitosan, or via liposomes. A preferred adjuvanted or non adjuvanted vaccine dose at the minimal protective dose through vaccine release may provide between approximately 10 and approximately $10^6$ $\log_{10}TCID_{50}$ of virus per dose, or higher. "TCID50" refers to "tissue culture infective dose" and is defined as that dilution of a virus required to infect 50% of a given batch of inoculated cell cultures. Various methods may be used to calculate TCID50, including the Spearman-Karber method which is utilized throughout this specification. For a description of the Spearman-Karber method, see B. W. Mahy & H. O. Kangro, Virology Methods Manual, p. 25-46 (1996). Adjuvants, if present, may be provided as emulsions, more commonly if non-oral administration is selected, but should not decrease starting titer by more than 0.7 logs (80% reduction).

In one example, adjuvant components are provided from a combination of lecithin in light mineral oil, and also an aluminum hydroxide component. Details concerning the composition and formulation of Amphigen® (as representative lecithin/mineral oil component) are as follows.

A preferred adjuvanted may be provided as a 2 ML dose in a buffered solution further comprising about 5% (v/v) Rehydragel® (aluminum hydroxide gel) and "20% Amphigen"® at about 25% final (v/v). Amphigen® is generally described in U.S. Pat. No. 5,084,269 and provides de-oiled lecithin (preferably soy) dissolved in a light oil, which is then dispersed into an aqueous solution or suspension of the antigen as an oil-in-water emulsion. Amphigen has been improved according to the protocols of U.S. Pat. No. 6,814, 971 (see columns 8-9 thereof) to provide a so-called "20% Amphigen" component for use in the final adjuvanted vaccine compositions of the present invention. Thus, a stock mixture of 10% lecithin and 90% carrier oil (DRAKEOL®, Penreco, Karns City, Pa.) is diluted 1:4 with 0.63% phosphate buffered saline solution, thereby reducing the lecithin and DRAKEOL components to 2% and 18% respectively (i.e. 20% of their original concentrations). Tween 80 and Span 80 surfactants are added to the composition, with representative and preferable final amounts being 5.6% (v/v) Tween 80 and 2.4% (v/v) Span 80, wherein the Span is originally provided in the stock DRAKEOL component, and the Tween is originally provided from the buffered saline component, so that mixture of the saline and DRAKEOL components results in the finally desired surfactant concentrations. Mixture of the DRAKEOL/lecithin and saline solutions can be accomplished using an In-Line Slim Emulsifier apparatus, model 405, Charles Ross and Son, Hauppauge, N.Y., USA.

The vaccine composition also includes Rehydragel® LV (about 2% aluminum hydroxide content in the stock material), as additional adjuvant component (available from Reheis, N.J., USA, and ChemTrade Logistics, USA). With further dilution using 0.63% PBS, the final vaccine composition contains the following compositional amounts per 2 ML dose; 5% (v/v) Rehydragel® LV; 25% (v/v) of "20% Amphigen", i.e. it is further 4-fold diluted); and 0.01% (w/v) of merthiolate.

As is understood in the art, the order of addition of components can be varied to provide the equivalent final vaccine composition. For example, an appropriate dilution of virus in buffer can be prepared. An appropriate amount of Rehydragel® LV (about 2% aluminum hydroxide content) stock solution can then be added, with blending, in order to permit the desired 5% (v/v) concentration of Rehydragel® LV in the actual final product. Once prepared, this intermediate stock material is combined with an appropriate amount of "20% Amphigen" stock (as generally described above, and already containing necessary amounts of Tween 80 and Span 80) to again achieve a final product having 25% (v/v) of "20% Amphigen". An appropriate amount of 10% merthiolate can finally be added.

The vaccinate compositions of the invention permit variation in all of the ingredients, such that the total dose of antigen may be varied preferably by a factor of 100 (up or down) compared to the antigen dose stated above, and most preferably by a factor of 10 or less (up or down). Similarly, surfactant concentrations (whether Tween or Span) may be varied by up to a factor of 10, independently of each other, or they may be deleted entirely, with replacement by appropriate concentrations of similar materials, as is well understood in the art.

Rehydragel® concentrations in the final product may be varied, first by the use of equivalent materials available from many other manufacturers (i.e. Alhydrogel®, Brenntag; Denmark), or by use of additional variations in the Rehydragel® line of products such as CG, HPA or HS. Using LV as an example, final useful concentrations thereof including from 0% to 20%, with 2-12% being more preferred, and 4-8% being most preferred, Similarly, the although the final concentration of Amphigen (expressed as % of "20% Amphigen") is preferably 25%, this amount may vary from 5-50%, preferably 20-30% and is most preferably about 24-26%.

According to the practice of the invention, the oil used in the adjuvant formulations of the instant invention is preferably a mineral oil. As used herein, the term "mineral oil" refers to a mixture of liquid hydrocarbons obtained from petrolatum via a distillation technique. The term is synonymous with "liquefied paraffin", "liquid petrolatum" and "white mineral oil." The term is also intended to include "light mineral oil," i.e., oil which is similarly obtained by distillation of petrolatum, but which has a slightly lower specific gravity than white mineral oil. See, e.g., Remington's Pharmaceutical Sciences, 18th Edition (Easton, Pa.: Mack Publishing Company, 1990, at pages 788 and 1323). Mineral oil can be obtained from various commercial sources, for example, J. T. Baker (Phillipsburg, Pa.), USB Corporation (Cleveland, Ohio). Preferred mineral oil is light mineral oil commercially available under the name DRAKEOL®.

Typically, the oily phase is present in an amount from 50% to 95% by volume; preferably, in an amount of greater than 50% to 85%; more preferably, in an amount from greater than 50% to 60%, and more preferably in the amount of greater than 50-52% v/v of the vaccine composition. The oily phase includes oil and emulsifiers (e.g., SPAN® 80, TWEEN® 80 etc), if any such emulsifiers are present.

Non-natural, synthetic emulsifiers suitable for use in the adjuvant formulations of the present invention also include sorbitan-based non-ionic surfactants, e.g. fatty-acid-substituted sorbitan surfactants (commercially available under the name SPAN® or ARLACEL®), fatty acid esters of polyethoxylated sorbitol (TWEEN®), polyethylene glycol esters of fatty acids from sources such as castor oil (EMULFOR®); polyethoxylated fatty acid (e.g., stearic acid available under the name SIMULSOL® M-53), polyethoxylated isooctylphenol/formaldehyde polymer (TYLOXAPOL®), polyoxyethylene fatty alcohol ethers (BRIJ®); polyoxyethylene nonphenyl ethers (TRITON® N), polyoxyethylene isooctylphenyl ethers (TRITON® X). Preferred synthetic surfactants are the surfactants available under the name SPAN® and TWEEN®, such as TWEEN®-80 (Polyoxyethylene (20) sorbitan monooleate) and SPAN®-80 (sorbitan monooleate). Generally speaking, the emulsifier(s) may be present in the vaccine composition in an amount of 0.01% to 40% by volume, preferably, 0.1% to 15%, more preferably 2% to 10%.

In an alternative embodiment of the invention, the final vaccine composition contains SP-Oil® and Rehydragel® LV as adjuvants (or other Rehydragel® or Alhydrogel® products), with preferable amounts being about 5-20% SP-Oil (v/v) and about 5-15% Rehydragel LV (v/v), and with 5% and 12%, respectively, being most preferred amounts. In this regard it is understood that % Rehydragel refers to percent dilution from the stock commercial product. (SP-Oil® is a fluidized oil emulsion with includes a polyoxyethylene-polyoxypropylene block copolymer (Pluronic® L121, BASF Corporation, squalene, polyoxyethylene sorbitan monooleate (Tween®80, ICI Americas) and a buffered salt solution.)

It should be noted that the present invention may also be successfully practiced using wherein the adjuvant component is only Amphigen®.

In another embodiment of the invention, the final vaccine composition contains TXO as an adjuvant; TXO is generally described in WO 2015/042369. All TXO compositions disclosed therein are useful in the preparation of vaccines of the invention. In TXO, the immunostimulatory oligonucleotide ("T"), preferably an ODN, preferably containing a palindromic sequence, and optionally with a modified backbone, is present in the amount of 0.1 to 5 ug per 50 ul of the vaccine composition (e.g., 0.5-3 ug per 50 ul of the composition, or more preferably 0.09-0.11 ug per 50 ul of the composition). A preferred species thereof is SEQ ID NO: 8 as listed (page 17) in the WO2015/042369 publication (PCT/US2014/056512). The polycationic carrier ("X") is present in the amount of 1-20 ug per 50 ul (e.g., 3-10 ug per 50 ul, or about 5 ug per 50 ul). Light mineral oil ("O") is also a component of the TXO adjuvant.

In certain embodiments, TXO adjuvants are prepared as follows:

a) Sorbitan monooleate, MPL-A and cholesterol are dissolved in light mineral oil. The resulting oil solution is sterile filtered;

b) The immunostimulatory oligonucleotide, Dextran DEAE and Polyoxyethylene (20) sorbitan monooleate are dissolved in aqueous phase, thus forming the aqueous solution; and c) The aqueous solution is added to the oil solution under continuous homogenization thus forming the adjuvant formulation TXO.

All the adjuvant compositions of the invention can be used with any of the PSV strains and isolates covered by the present Specification.

Additional adjuvants useful in the practice of the invention include Prezent-A (see generally United States published patent application US20070298053; and "QCDCRT" or "QCDC"-type adjuvants (see generally United States published patent application US20090324641.

Excipients

The immunogenic and vaccine compositions of the invention can further comprise pharmaceutically acceptable carriers, excipients and/or stabilizers (see e.g. Remington: The Science and practice of Pharmacy, 2005, Lippincott Williams), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as Mercury((o-carboxyphenyl)thio)ethyl sodium salt (THIOMERSAL), octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG), TWEEN or PLURONICS.

Vaccines of the present invention can optionally be formulated for sustained release of the virus, infectious DNA molecule, plasmid, or viral vector of the present invention. Examples of such sustained release formulations include virus, infectious DNA molecule, plasmid, or viral vector in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279-292, which is incorporated herein by reference. Additional guidance in selecting and using polymers in pharmaceutical formulations can be found in texts known in the art, for example M. Chasin and R. Langer (eds), 1990, "Biodegradable Polymers as Drug Delivery Systems" in: Drugs and the Pharmaceutical Sciences, Vol. 45, M. Dekker, N.Y., which is also incorporated herein by reference. Alternatively, or additionally, the virus, plasmid, or viral vector can be microencapsulated to improve administration and efficacy. Methods for microencapsulating antigens are well-known in the art, and include techniques described, e.g., in U.S. Pat. Nos. 3,137,631; 3,959,457; 4,205,060; 4,606,940; 4,744,933; 5,132,117; and International Patent Publication WO 95/28227, all of which are incorporated herein by reference.

Liposomes can also be used to provide for the sustained release of virus, plasmid, viral protein, or viral vector. Details concerning how to make and use liposomal formulations can be found in, among other places, U.S. Pat. Nos. 4,016,100; 4,452,747; 4,921,706; 4,927,637; 4,944,948; 5,008,050; and 5,009,956, all of which are incorporated herein by reference.

An effective amount of any of the above-described vaccines can be determined by conventional means, starting with a low dose of virus, viral protein plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies.

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above.

The effective dose amount of virus, protein, infectious nucleotide molecule, plasmid, or viral vector, of the present invention can be determined using known techniques, taking into account factors that can be determined by one of ordinary skill in the art such as the weight of the animal to be vaccinated. The dose amount of virus of the present invention in a vaccine of the present invention preferably ranges from about $10^1$ to about $10^9$ pfu (plaque forming units), more preferably from about $10^2$ to about $10^8$ pfu, and most preferably from about $10^3$ to about $10^7$ pfu. The dose amount of a plasmid of the present invention in a vaccine of the present invention preferably ranges from about 0.1 µg to about 100 mg, more preferably from about 1 µg to about 10 mg, even more preferably from about 10 µg to about 1 mg. The dose amount of an infectious DNA molecule of the present invention in a vaccine of the present invention preferably ranges from about 0.1 µg to about 100 mg, more preferably from about 1 µg to about 10 mg, even more preferably from about 10 µg to about 1 mg. The dose amount of a viral vector of the present invention in a vaccine of the present invention preferably ranges from about $10^1$ pfu to about $10^9$ pfu, more preferably from about $10^2$ pfu to about $10^8$ pfu, and even more preferably from about $10^3$ to about $10^7$ pfu. A suitable dosage size ranges from about 0.5 ml to about 10 ml, and more preferably from about 1 ml to about 5 ml.

Suitable doses for viral protein or peptide vaccines according to the practice of the present invention range generally from 1 to 50 micrograms per dose, or higher amounts as may be determined by standard methods, with the amount of adjuvant to be determined by recognized methods in regard of each such substance. In a preferred example of the invention relating to vaccination of swine, an optimum age target for the animals is between about 1 and 21 days, which at pre-weening, may also correspond with other scheduled vaccinations such as against *Mycoplasma hyopneumoniae*. Additionally, a preferred schedule of vaccination for breeding sows would include similar doses, with an annual revaccination schedule.

Dosing

A preferred clinical indication is for treatment, control and prevention in both breeding sows and gilts pre-farrowing, followed by vaccination of piglets. In a representative example (applicable to both sows and gilts), two 2-ML doses of vaccine will be used, although of course, actual volume of the dose is a function of how the vaccine is formulated, with actual dosing amounts ranging from 0.1 to 5 ML, taking also into account the size of the animals. Single dose vaccination is also appropriate.

The first dose may be administered as early as pre-breeding to 5-weeks pre-farrowing, with the second dose administered preferably at about 1-3 weeks pre-farrowing. Doses vaccine preferably provide an amount of viral material that corresponds to a $TCID_{50}$ (tissue culture infective dose) of between about $10^6$ and $10^8$, more preferably between about $10^7$ and $5\times10^7$, and can be further varied, as is recognized in the art. Booster doses can be given two to four weeks prior to any subsequent farrowings. Intramuscular vaccination (all doses) is preferred, although one or more of the doses could be given subcutaneously. Oral administration is also preferred. Vaccination may also be effective in naïve animals, and non-naïve animals as accomplished by planned or natural infections.

In a further preferred example, the sow or gilt is vaccinated intramuscularly or orally at 5-weeks pre-farrowing and then 2-weeks pre-farrowing. Under these conditions, a protective immune response can be demonstrated in PSV-negative vaccinated sows in that they developed antibodies (measured via fluorescent focal neutralization titer from serum samples) with neutralizing activity, and these antibodies were passively transferred to their piglets. The protocols of the invention are also applicable to the treatment of already seropositive sows and gilts, and also piglets and boars. Booster vaccinations can also be given, and these may be via a different route of administration. Although it is preferred to re-vaccinate a mother sow prior to any subsequent farrowings, the vaccine compositions of the invention nonetheless can still provide protection to piglets via ongoing passive transfer of antibodies, even if the mother sow was only vaccinated in association with a previous farrowing.

It should be noted that piglets may then be vaccinated as early as Day 1 of life. For example, piglets can be vaccinated at Day 1, with or without a booster dose at 3 weeks of age, particularly if the parent sow, although vaccinated pre-breeding, was not vaccinated pre-farrowing. Piglet vaccination may also be effective if the parent sow was previously not naïve either due to natural or planned infection. Vaccination of piglets when the mother has neither been previously exposed to the virus, nor vaccinated pre-farrowing may also effective. Boars (typically kept for breeding purposes) should be vaccinated once every 6 months. Variation of the dose amounts is well within the practice of the art. It should be noted that the vaccines of the present invention are safe for use in pregnant animals (all trimesters) and neonatal swine. The vaccines of the invention are attenuated to a level of safety (i.e. no mortality, only transient mild clinical signs or signs normal to neonatal swine) that is acceptable for even the most sensitive animals again including neonatal pigs. Of course, from a standpoint of protecting swine herds both from PSV epidemics and persistent low-level PSV occurrence, programs of sustained sow vaccination are of great importance. It will be appreciated that sows or gilts immunized with PSV modified live virus (MLV) will passively transfer immunity to piglets, including PSV-specific IgA, which will protect piglets from PSV associated disease and mortality. Generally, pigs that are immunized with PSV MLV will have a decrease in amount and/or duration or be protected from shedding PSV in their feces, and further, pigs that are immunized with PSV MLV will be protected from weight loss and failure to gain weight due to PSV, and further, PSV MLV will aid in stopping or controlling the PSV transmission cycle.

It should also be noted that animals vaccinated with the vaccines of the invention are also immediately safe for human consumption, without any significant slaughter withhold, such as 21 days or less.

When provided therapeutically, the vaccine is provided in an effective amount upon the detection of a sign of actual infection. Suitable dose amounts for treatment of an existing infection include between about $10^1$ and about $10^6$ $\log_{10}TCID_{50}$, or higher, of virus per dose (minimum immunizing dose to vaccine release). A composition is said to be "pharmacologically acceptable" if its administration can be tolerated by a recipient. Such a composition is said to be administered in a "therapeutically or prophylactically effective amount" if the amount administered is physiologically significant.

At least one vaccine or immunogenic composition of the present invention can be administered by any means that achieve the intended purpose, using a pharmaceutical composition as described herein. For example, route of administration of such a composition can be by parenteral, oral, oronasal, intranasal, intratracheal, topical, subcutaneous, intramuscular, transcutaneous, intradermal, intraperitoneal, intraocular, and intravenous administration. In one embodiment of the present invention, the composition is administered by intramuscularly. Parenteral administration can be by bolus injection or by gradual perfusion over time. Any suitable device may be used to administer the compositions, including syringes, droppers, needleless injection devices, patches, and the like. The route and device selected for use will depend on the composition of the adjuvant, the antigen, and the subject, and such are well known to the skilled artisan. Administration that is oral, or alternatively, subcutaneous, is preferred. Oral administration may be direct, via water, or via feed (solid or liquid feed). When provided in liquid form, the vaccine may be lyophilized with reconstitution, pr provided as a paste, for direct addition to feed (mix in or top dress) or otherwise added to water or liquid feed.

Generation of Vero Cells Suitable for Large Scale Virus Production

Viruses of the invention may be grown in various cell stocks, such as but not limited to ST or IPEC-1 cell stocks. To generate safe and approved cell stock, a vial of cells may be subject to additional passaging. The cells may be passed one or more times in the appropriate medium, such as but not limited to MEM or more completely media such as but not limited to PMEM w/wheat to produce a Master Cell Stock (MCS). The MCS may be tested in accordance with 9 CFR & EP requirements in PGM-Biological Quality Control; Lincoln, Nebr. The MCS may be tested for satisfactory results in sterility, freedom from mycoplasmas, and extraneous agents.

As a nonlimiting example, seed origin and passage may be as follows. A frozen Pre-master Cell stock of cells is thawed. Cell stock may be prepared by growing the thawed cells in MEM or PMEM bovine serum and L-glutamine. The Pre-master cell stock may then be passaged a number of times, for example from about 1 to about 50 times, from about 10 to about 40 times, or from about 20 to about 30 times. All cultures may be grown in flacks, such as 25, 75, or 150 cm² T-Flasks. The flasks may be incubated in about 5.0% $CO_2$ at about 36° C. for about 5 days, for about 6 days, for about 7, for about 8 days, or more and then expanded. After flasks reach about 80%, about 90%, or about 100% confluency, the cultures may be passed into larger, such as 850 cm², roller bottles. Rollers may be incubated at about 36° C. at about 0.125 to about 0.250 rpm without $CO_2$. After a final passage, cryopreservation may be completed by adding about 8%, about 9%, about 10%, about 11% or about 12% bovine calf serum and about 8%, about 9%, about 10%, about 11%, or about 12% dimethyl sulfoxide (DMSO) to the condensed cell suspension. Containers containing about 4 ml of cells may then be placed into a controlled rate freezer and then transferred into liquid nitrogen tank for long term storage at vapor phase. Antibiotics may be used to produce the MCS.

Sterility Testing of the Master Cell Stock may be tested as per 9 CFR (026-ST0) and EP 2.6.1 to determine if the MCS is free of bacterial and fungal contamination.

*Mycoplasma* Testing and Extraneous Testing were accomplished of the MCS may be tested as per 9 CFR (028-PU0) and EP 2.6.7. Extraneous testing may also be completed as per 9 CFR 113.52 using NL-BT-2 (Bovine), Vero, NL-ED-5 (Equine), NL-ST-1 (Porcine), NL-DK (Canine), or NL-FK (Feline) cells. The MCS may be checked to determine if it is negative for MGG, CPE and HAd and tested by FA for BVD, BRSV, BPV, BAV-1, BAV-5, Rabies, Reo, BTV, ERV, Equine arteritis, PPV, TGE, PAV, HEV, CD, CPV, FPL and FIP. The MCS may further be tested by ELISA for other contaminates such as, but not limited to, FIV. Additionally, the MCS may be tested for BCV, BVDV, CSF, HPS, IAV, IBRV, HMP, MHR, MHS, PCV, PDCV, PEDV, PRCV, PRRSV, PRV, or SVA.

EP extraneous testing was as per 5.2.4 (52-2002) for extraneous testing may use Bovine NL-BT-2 and EBK (Primary), Vero, NL-ED-5 (Equine), NL-ST-1 (Porcine), MARC MA 104, NL-DK (Canine) NL-FK(Feline) cells to test for for MGG, CPE, HAd and tested by FA for BVD, BPV, BAV-1, BAV-5, Bovine corona, Bovine rotavirus, BHV-3, PI3, IBR, BRSV and BEV-1, Reo, BTV, ERV, Equine arteritis, PPV, PRV, TGE, HEV, PAV, P. rota A1, rota A2, PRRSV, CD, CPI, CAV-2, Measles, C. rota, Rabies, CCV, FP, FCV, FVR, FIP and FeLV.

Polypeptides and Polynucleotides of the Invention

Representative embodiments of the invention include an isolated polynucleotide sequence that comprises a polynucleotide selected from the group consisting of: (a) SEQ ID NOs: 1, 2; or a fragment thereof; (b) the complement of any sequence in (a); (c) a polynucleotide that hybridizes with a sequence of (a) or (b) under stringent conditions defined as hybridizing to filter bound DNA in 0.5M $NaHPO_4$, 7% SDS, 1 mM EDTA at 65° C., and washing in 0.1×SSC/0.1% SDS at 68° C.; (d) a polynucleotide that is at least 70% identical to the polynucleotide of (a) or (b); (e) a polynucleotide that is at least 80% identical to the polynucleotide of (a) or (b); (f) a polynucleotide that is at least 90% identical to the polynucleotide of (a) or (b); and (g) a polynucleotide that is at least 95% identical to the polynucleotide of (a) or (b). In a preferred embodiment the polynucleotide includes a second heterologous polynucleotide sequence.

The invention also provides a polypeptide encoded by the open reading frames of the genotype of SEQ ID NOs: 1, 2, combinations thereof, or a polypeptide that is at least 90% identical thereto, domains thereof, or to a fragment thereof, including the option that additional otherwise identical amino acids are replaced by conservative substitutions.

The invention also provides a polypeptide encoded by the open reading frame of the variant PSV strain of the invention or a polypeptide that is at least 90% identical thereto, or to a fragment thereof, including the option that additional otherwise identical amino acids are replaced by conservative substitutions.

In a further preferred embodiment, there are further provided PSV polypeptide-based vaccines wherein the antigen is defined by: a protein encoded by the open reading frame of SEQ ID NOs: 1, 2, combinations thereof, or an immunogenic fragment thereof.

Further Genetic Manipulations

The polynucleotide and amino acid sequence information provided by the present invention also makes possible the systematic analysis of the structure and function of the viral genes and their encoded gene products. Knowledge of a polynucleotide encoding a viral gene product of the invention also makes available anti-sense polynucleotides which recognize and hybridize to polynucleotides encoding a polypeptide of the invention, or a fragment thereof. Full length and fragment anti-sense polynucleotides are useful in this respect. The worker of ordinary skill will appreciate that fragment anti-sense molecules of the invention include (i) those which specifically recognize and hybridize to a specific RNA (as determined by sequence comparison of DNA encoding a viral polypeptide of the invention as well as (ii) those which recognize and hybridize to RNA encoding variants of the encoded proteins. Antisense polynucleotides that hybridize to RNA/DNA encoding other PSV peptides are also identifiable through sequence comparison to identify characteristic, or signature sequences for the family of molecules, further of use in the study of antigenic domains in PSV polypeptides, and may also be used to distinguish between infection of a host animal with remotely related non-PSV members of the Picornaviridae.

Guidance for effective codon optimization for enhanced expression in yeast and *E. coli* for the constructs of the invention is generally known to those of skill in the art.

Antibodies

Also contemplated by the present invention are anti-PSV antibodies (e.g., monoclonal and polyclonal antibodies, single chain antibodies, chimeric antibodies, humanized, human, porcine, and CDR-grafted antibodies, including compounds which include CDR sequences which specifically recognize a PSV polypeptide of the invention. The term "specific for" indicates that the variable regions of the antibodies of the invention recognize and bind a PSV polypeptide exclusively (i.e., are able to distinguish a single PSV polypeptide from related polypeptides despite sequence identity, homology, or similarity found in the family of polypeptides), and which are permitted (optionally) to interact with other proteins (for example, *S. aureus* protein A or other antibodies in ELISA techniques) through interactions with sequences outside the variable region of the antibodies, and in particular, in the constant region of the Ab molecule. Screening assays to determine binding specificity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies that recognize and bind fragments of the PSV polypeptides of the invention are also contemplated, provided that the antibodies are first and foremost specific for, as defined above, a PSV polypeptide of the invention from which the fragment was derived.

For the purposes of clarity, "antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions.

Antibodies can exist in a variety of forms including, for example, as, Fv, Fab, F(ab')$_2$, monospecific Fab$_2$, bispecific Fab$_2$, trispecific Fab$_3$, monovalent IgG, scFv, bispecific diabody, trispecific triabody, scFv-Fc, or minibody, as well as in single chains, and include synthetic polypeptides that contain all or part of one or more antibody single chain polypeptide sequences.

An immunoglobulin or its encoding cDNA may be further modified. Thus, in a further embodiment the method of the present invention comprises any one of the step(s) of producing, for example, a chimeric antibody, porcinized, murinized, or humanized antibody, single-chain antibody, Fab-fragment, bispecific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor (1988). When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO89/09622. Methods for the production of humanized antibodies are described in, e.g., European application EP-A1 0 239 400 and international application WO90/07861. A further source of antibodies to be utilized in accordance with the present invention are so-called xenogeneic antibodies. The general principle for the production of xenogeneic antibodies such as human-like antibodies in mice is described in, e.g., international applications WO91/10741, WO94/02602, WO96/34096 and WO 96/33735. As discussed above, the antibody of the invention may exist in a variety of forms besides complete antibodies; including, for example, Fv, Fab and F(ab)$_2$, as well as in single chains; see e.g. international application WO88/09344.

Diagnostic Kits

The present invention also provides diagnostic kits. The kit can be valuable for differentiating between porcine animals naturally infected with a field strain of a PSV virus and porcine animals vaccinated with any of the PSV vaccines described herein. The kits can also be of value because animals potentially infected with field strains of PSV virus can be detected prior to the existence of clinical symptoms and removed from the herd or kept in isolation away from naive or vaccinated animals. The kits include reagents for analyzing a sample from a porcine animal for the presence of antibodies to a particular component of a specified PSV virus. Diagnostic kits of the present invention can include as a component a peptide or peptides from the variant PSV strain of the invention which is present in a field strain but not in a vaccine of interest, or vice versa, and selection of such suitable peptide domains is made possible by the extensive amino acid sequencing. As is known in the art, kits of the present invention can alternatively include as a component a peptide which is provided via a fusion protein. The term "fusion peptide" or "fusion protein" for purposes of the present invention means a single polypeptide chain consisting of at least a portion of a PSV virus protein.

The invention includes the following embodiments. An isolated Porcine *Sapelovirus* (PSV) encoded by a DNA polynucleotide of a sequence for US/ISU26908B/18.

The virus US/ISU26908B/18 wherein said sequence for US/ISU26908B/18 is defined as a DNA polynucleotide encoding said virus is at least 95%, 98%, 99%, or 99.5% identical, at a full-length nucleotide level, to SEQ ID NO: 2.

A vaccine composition comprising a porcine *Sapelovirus* (PSV) US/ISU26908B/18, and a carrier, wherein said composition is capable of protecting swine from challenge by both variant and prototype strains of PSV and preventing or treating one or more symptoms associated with PSV infection, and wherein achievement of protection is determined by an endpoint selected from the group consisting of prevention or control of any of the PSV infection symptoms diarrhea, skin lesions, myelitis, polioencephalomyelitis with ataxia and eventual limb paralysis, reproductive failure (SMEDI syndrome), atypical neurologic disease, and mortality.

The vaccine composition wherein the virus is live or killed.

The vaccine composition wherein said carrier is a diluent.

The vaccine composition further comprising an adjuvant.

The vaccine composition wherein said protected swine include any of sows, gilts, boars, hogs, and piglets.

The vaccine composition wherein said vaccine is effective in a single dose program or a two-dose program.

The vaccine composition, wherein the first dose is administered when the piglet is about 1-7 days old, and the second dose is administered when the piglet is 2-5 weeks old.

The vaccine composition, wherein the single dose is administered at about 1-21 days old, preferably at about 1-7 days old.

The vaccine composition, wherein the minimum effective dose is between about $10^1$ and about $10^6$ $\log_{10}$ $TCID_{50}$.

The vaccine composition wherein the adjuvant is de-oiled lecithin dissolved in an oil, usually light liquid paraffin and aluminum hydroxide, or CpG/DEAE-dextran/mineral oil (TXO).

A method of treating or preventing disease in a piglet caused by PSV, comprising administering to said piglet a first dose of the vaccine composition when said piglet is about 1-7 days old.

The method wherein said administering further includes administering a second dose of said vaccine when the piglet is about 2-5 weeks old.

The method, wherein 2 doses are administered to the piglet, and the parent sow, although vaccinated pre-breeding, was not vaccinated pre-farrowing.

The method, wherein 2 doses are administered to the piglet, and the parent sow is vaccinated pre-farrowing.

A method of treating or preventing disease in a piglet caused by porcine *Sapelovirus* (PSV), comprising administering to said piglet a single effective dose of the vaccine composition when said piglet is about 1-7 days old, wherein the mother sow is naïve to PSV, and is not, at any time, vaccinated.

A full-length RNA polynucleotide that corresponds to the encoding DNA polynucleotide of US/ISU26908B/18, or the complement thereof.

The RNA polynucleotide that is an infectious clone.

A plasmid or bacterial artificial chromosome that comprises the encoding DNA polynucleotide US/ISU26908B/18.

A live attenuated virus composition, comprising:
a variant strain porcine *Sapelovirus* (PSV); and
a carrier.

The live attenuated virus composition, wherein said variant strain porcine *Sapelovirus* (PSV) is US/ISU26908B/18.

The virus US/ISU26908B/18, wherein said sequence for US/ISU26908B/18 is defined as a DNA polynucleotide encoding said virus is at least 95%, 98%, 99%, or 99.5% identical, at a full-length nucleotide level, to SEQ ID NO: 2.

A vaccine composition comprising a live attenuated variant porcine epidemic *Sapelovirus* (PSV) and a carrier wherein said strain is encoded by a sequence of US/ISU26908B/18, wherein said composition is capable of protecting swine from challenge by both variant and prototype strains of PSV and preventing or treating one or more symptoms associated with PSV infection, and wherein said protection is assessed by an endpoint selected from the group consisting of diarrhea, skin lesions, myelitis, polioencephalomyelitis with ataxia and eventual limb paralysis, reproductive failure (SMEDI syndrome), atypical neurologic disease, and mortality.

The vaccine composition wherein said carrier is a diluent.

The vaccine composition wherein said diluent is a sterile diluent.

The vaccine composition further comprising an adjuvant.

The vaccine composition wherein said protected swine include any of sows, gilts, boars, hogs, and piglets.

The vaccine composition, which is effective in piglets that are 1 day of age or older.

The vaccine composition wherein said vaccine is effective in a single dose program.

The vaccine composition wherein said vaccine is effective in a two dose program.

The vaccine composition, wherein the first dose is administered when the piglet is about 1-7 days old, and the second dose is administered when the piglet is 2-5 weeks old.

The vaccine composition, wherein the minimum effective dose is between about $10^1$ and about $10^6$ $\log_{10}$ $TCID_{50}$.

The vaccine composition wherein the adjuvant is de-oiled lecithin dissolved in an oil, usually light liquid paraffin and aluminum hydroxide.

The vaccine composition, wherein said adjuvant is CpG/DEAE-dextran/mineral oil (TXO).

A method of treating or preventing disease in a piglet caused by PSV, comprising administering to said piglet a first dose of the vaccine composition when said piglet is about 1-7 days old, and optionally, administering a second dose of said vaccine when the piglet is about 2-5 weeks old.

The method, wherein 2 doses are administered to the piglet, and the parent sow, although vaccinated pre-breeding, was not vaccinated pre-farrowing.

The method, wherein 1 dose is administered to the piglet, and the parent sow, was vaccinated both pre-breeding and pre-farrowing.

A method of treating or preventing disease in a piglet caused by PSV, comprising first administering the vaccine composition to the sow of said piglet pre-farrowing or pre-breeding, following by administering one or more doses of said vaccine composition to said piglet after birth.

A method of preventing disease in healthy pigs caused by PSV, comprising first vaccinating said pigs with the vaccine composition, followed by annual or pre-farrowing administration of further doses of inactivated PSV vaccine.

The composition wherein said variant indel strain is more virulent in 3 week old pigs, but less virulent in 7 week old pigs.

A method of preventing disease in healthy pigs caused by PSV, comprising first vaccinating said pigs with a prototype attenuated live PSV vaccine composition in 3 week old pigs followed by a second vaccination at week 7 or older pigs with a vaccine composition.

A binding molecule for porcine *Sapelovirus* (SPV), comprising one or more complementary determining regions (CDRs) recognizing epitopes on one or more polypeptides encoded by a sequence of US/ISU26908B/18 or a fragment thereof.

The binding molecule, wherein said binding molecule is an antibody or a fragment, variant, or derivative thereof.

The antibody fragment, wherein said antibody fragment, variant, or derivative is selected from the group comprising: Fab, F(ab')$_2$, monospecific Fab$_2$, bispecific Fab$_2$, trispecific Fab$_3$, monovalent IgG, scFv, bispecific diabody, trispecific triabody, scFv-Fc, or minibody.

The antibody, wherein said antibody is porcinized, humanized. murinized, or chimeric.

A polynucleotide encoding the antibody polypeptide.

An expression vector, comprising:
one or more polynucleotides; and
a promoter, wherein said one or more polynucleotides is operantly linked to said promoter.

The promoter, wherein said promoter is an eukaryote promoter.

A bacterial host cell transformed with the expression vector

The promoter wherein said promoter is a heterologous promoter.

The expression vector, wherein said expression vector is a plasmid, phage, virus, or retrovirus.

A host cell, comprising an expression vector.

The host cell, wherein said host cell is mammalian.

A kit for detecting the presence of anti-PSV antibodies, comprising:
one or more PSV polypeptides with at least 90% identity to one or more polypeptides encoded by a sequence of US/ISU26908B/18 or fragment thereof; and
a set of reagents.

The one or more polypeptides, wherein said one or more polypeptides is found in a field strain but not a vaccine.

The one or more polypeptides, wherein said one or more polypeptides is found in a vaccine but not in a field strain.

The kit of 63, wherein the sequence of US/ISU26908B/18 is defined as SEQ ID NO: 2.

The sequence of US/ISU26908B/18, wherein said sequence for US/ISU26908B/18 is defined as a DNA polynucleotide encoding said virus is at least 95%, 98%, 99%, or 99.5% identical, at a full-length nucleotide level, to SEQ ID NO: 2.

The sequence of or protein encoded by US/ISU26908B/18 or fragment thereof of which includes one or more of the following features: a) a TTT inserted at position 3,006; b) a G to A SNP at position 1,318;
c) an A to G SNP at position 2,360; d) a C to T SNP at 2,793; e) an A to G SNP at 4,154; and/or f) a G to A SNP at 6,115.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

As no strain has yet been adopted for a purified cell culture system, prototype strains had to be first isolated. For initial isolation, two, seven-week-old pigs (A and B) exhibiting from limb ataxia were euthanized and spinal cord samples were sent for general diagnostics for gross pathology, histopathology, and ancillary diagnostics using standard diagnostic techniques.

The gross pathology of the spinal cord samples showed no grow lesions along the spinal cords, muscles or bone of submitted spinal columns. The histopathology showed that both pigs A and B had nonsuppurative myelitis. The ancillary diagnostics tests showed both pigs A and B had PSV in both of their spinal cords at clinically relevant levels by real time PCR. Additionally, pig A may have had a low amount of porcine teschovirus (PTV) as determined by real time PCR, while pig B may have had a low amount of *Steptococcus suis* as determined by culture followed by hematoxylin and eosin assays.

These results indicated that both pig A and B had viral myelitis caused by PSV, making strains isolated from pig A and B good targets for creating an isolate adapted for cell culture.

Example 2

To create the adapted isolate, six different strains, US/ISU26908B/18; US/ISU20472B; US/ISU61750A; US/ISU61750G; US/ISU61750F; and US/ISU66822, extracted from brain or spinal cord were grown on different cell lines, ST, PK-15, and Vero cells. Each strain was grown on each cell line for a total of 18 combinations.

The combinations were made by prepping each tissue sample, and then filtering 200 μL onto each cell line and incubated at 36° C. in a 5% CO$_2$ atmosphere for four hours. After 4 hours, cell lines were washed and then incubated in 1 mL MEM supplemented with 10% fetal bovine serum (FBS) and L-glutamate. The different strain by cell type combinations were then passaged with just MEM without any supplements. Part of passage 2 was assayed by real time PCR for the presence of strains on each cell type, while the rest was used for future passages.

Strains US/ISU26908B/18 and US/ISU66822 showed presence on each of the cell lines while US/ISU61750A showed a low level of grown on only PK-15 cells. Strain US/ISU26908B/18 showed the highest amount of growth on ST cells. Passage 3 was further tested by real time PCR for the presence of various strains in select cell lines, specifically US/ISU26908B/18 on ST, PK-15, and Vero, US/ISU66822 on ST, PK-15, and Vero. As in passage 2, US/ISU26908B/18 on ST showed the highest growth, with US/ISU66822 on PK-15 showing some growth. No growth was detected on the other combinations. Passage 4 for US/ISU26908B/18 on ST was further tested, with US/ISU26908B/18 detected in the cell line. The ST cell line growing US/ISU26908B/18 was carried out past passage 10, and US/ISU26908B/18 continued to be detected.

In order to ensure the ST cell cultures were free of contaminants, they were tested for possible viral and bacterial contamination. This PSV isolate (ST cell passage 7) is free of rotavirus type A, B, or C, atypical porcine pestivirus (APPV), porcine epidemic diarrhea virus (PEDV), transmissible gastroenteritis virus (TGEV), porcine deltacoronavirus (PDCoV), Porcine *Enterovirus* (PEV), Porcine Teschovirus (PTV), senecavirus A (SVA) as confirmed by specific PCRs and high-throughput sequencing As strain US/ISU26908B/18 showed the best growth in cell culture, it was also tested on IPEC-1 cells. IPEC-1 cells were passaged at least ten times with US/ISU26908B/18, showing positive growth after the tenth passage.

Therefore, US/ISU26908B/18, unlike other strains, is capable of growing on various cell cultures through multiple passages.

Example 3

As passaging viruses during cell culture may result in changes to their sequence, it is important to determine if after long passages the genomes of the virus remains similar to the genome of the prototype.

The complete genomes of strain US/ISU26908B/18 was determined. The determined genomic sequences of virus passage 7 on ST cells is 7,556 nt in length, which remained 99.9% identical to the virus sequence determined from the original spinal cord tissue. This indicate this virus isolate is genetically stable on ST cell line.

The genome of strain US/ISU26908B/18 at passage 7 varied from the isolated strain throughout the polypeptide. Differences were one insertion and five single nucleotide polymorphisms (SNPs) The insertion was a 3-nt "TTT" at position 3,006. The SNPs include a G to A at position 1,318, an A to G at position 2,360, a C to T at position 2,793, an A to G at position 4,154, and a G to A at position 6,115.

As US/ISU26908B/18 is genetically stable on ST cells, it may be used for further modifications for the creations of immunizations or be used to create antibodies in various species for additional uses.

We claim:

1. An attenuated Porcine *sapelovirus* (PSV) encoded by a DNA polynucleotide that is SEQ ID NO:2 or a sequence that is at least 95% identical, at a full-length nucleotide level, to SEQ ID NO: 2 and where said sequence is not wild-type.

2. The sequence of claim 1 or fragment thereof of which include one or more of the following features:
   a) a TTT inserted at position 3,006;
   b) a G to A SNP at position 1,318;
   c) an A to G SNP at position 2,360;
   d) a C to T SNP at 2,793;
   e) an A to G SNP at 4,154; and/or
   f) a G to A SNP at 6,115.

3. The PSV polynucleotide of claim 1 in a plasmid or bacterial artificial chromosome.

4. The PSV polynucleotide of claim 1; and a promoter, wherein said one or more polynucleotides is operantly linked to said promoter to create an expression vector.

5. The expression vector of claim 4 in a host cell.

6. The expression vector of claim 4, wherein said expression vector is a plasmid, phage, virus, or retrovirus.

7. The DNA polynucleotide of claim 1 transcribed to a full-length RNA polynucleotide that corresponds thereto.

8. An immunogenic composition comprising a porcine *sapelovirus* (PSV) according to claim 1.

9. The immunogenic composition of claim 8 wherein the virus is live or killed.

10. The immunogenic composition of claim 8 wherein said carrier is a diluent.

11. The immunogenic composition of claim 8 further comprising an adjuvant.

12. The immunogenic composition of claim 11 wherein the adjuvant is de-oiled lecithin dissolved in an oil, usually light liquid paraffin and aluminum hydroxide.

13. The immunogenic composition of claim 11, wherein said adjuvant is CpG/DEAE-dextran/mineral oil (TXO).

14. A method for inducing an immune response against porcine *sapelovirus* (PSV) in swine, the method comprising:
administering to a swine the immunogenic composition of claim 8.

15. The method of claim 14, wherein the virus is live or killed.

16. The method of claim 14, wherein the carrier is a diluent.

17. The method of claim 14, wherein the composition further comprises an adjuvant.

18. The method of claim 14, wherein the swine include any of sows, gilts, boars, hogs, and piglets.

* * * * *

SEQUENCE LISTING

<160> NUMBER OF SEQ ID NOS: 2

<210> SEQ ID NO 1
<211> LENGTH: 7546
<212> TYPE: DNA
<213> ORGANISM: Porcine Sapelovirus

<400> SEQUENCE: 1

```
ggggtacatg cgtattacgg tacgcatgta ttccacactc atttccccccc tccaccctta      60 aggtggttgt atccccatac ctcaccctcc cttccacaca ggacggatac ttggacttgg     120
acccacggcg agaacatatg gtatggcttt tggatacgga tgaatggcag tagcgtggcg     180
agctatggaa aaatcgcaat tgtcgatagc catgttagtg acgcgcctcg gcgtgctcct     240
ttggtgattc ggcgactggt tacaggagag taggcagtga gctatgggca aacctctgca     300
gtattactca gagggaatgt gcaattgaga cttgacgagc gtctctttga gatgtggcgc     360
atgctcttgg cattaccata gtgagcttcc aggttgggaa acctggactg ggcctatact     420
acctgatagg gtcgcggctg gccgcctgta actagtatag tcagttgaaa cccccccatgg     480 aatctactac tactctttca ttttgcaact ggatccctaa gaaacagaga gcccgtgtgt     540
accttaccac cagtgtaaca cacgagaaat caagtggacc ctacacatat gtagtgtctg     600
acatgatcat gaaagaaaac agtagaacct ccccttgctat ggctttcgta gaagggaaga     660
cacttgtgtt caacaccggc acacaattgg gacaagttca ttcagctaac acaggcaata     720
aacctcaagg agcatacaac catggctccg gtagtattac acaaataaac tactatggtt     780
ctgattactc ccaagcatgg aatcctacac aacagcaaat ggaccectcc cagttcacca     840 aaccagtgac tgaaatagcc aatgcaatgg caggaccatc tctcaaggca cctgacaagg     900
aagaagaagg gtacagtgat aggttaatgc aattgacagc aggaaactcc tgtataacaa     960
cacaagaagc agctaaagca gttgtagcat atggacaatg gccaagttat aacatagatg    1020
caggagaaca tctagatctt gctacaactc cagggacagc agtggacagg ttttacacct    1080
ttgacagctt aagatggacc gacacacaag tcggtgaatg gtctctgcca ctgcctggtg    1140
gtttgatgga cacaggcgtg tttggtcaaa acctaagatt ccactacctc tccaggatgg    1200
gcttttgtgt acatgtacag tgcaatgcat caaaattcca ccagggtgca ctcatagttg    1260
caatgatacc agagcatcaa acacctaccc aagtgagtaa cgggtttgag tatagaagtg    1320
gagtgaccta ccagggaaac aattatccaa ctgaacaact acctatattt ccacaccaga    1380
ttataaacct gaggaccaac aactctgcaa caatagtcta tccatatacc aattgtactc    1440
cagcaggatt tggtttagca cacaactttg tcaccctggt tattagggtt ttagtgccac    1500
tcaagtacaa tacaggtgct tcaacttttg ttcctattac tgttagtgtg gcccccaatgt    1560
```

```
gttcacagtt tgcaggattg agatcagcag taacaagaca gggttttcct gttaggcagg    1620
taccaggcag ccaacaattt atgacaacac aaagagatag tgggatacca atctacccag    1680
agtttcagaa acccataat ttcaaattgc ccggaagggt aaccaatttg ctacaagttg    1740
ctcaggtggg gacctttctc aaatttagta attctacaaa cgacaccaat agaatctatt    1800
tgaatttgga tattacacag ggtgaccagt catcaaggat ggtggctatt gatgttagca    1860
tggtttcagc ccacttgtcc accacatacc tttcacggtt ggcacagatg tatgccaatt    1920
acaggggttc tgttgttttt gagtttatgt tttgtggtag ccagatggcc actgggaaac    1980
tactgatagc atacacacct cctggtggca cttcccccac aactaggact gatgcaatgt    2040
tggcaacaca tgttatttgg gatataggtt tacagtccac atgtaaaatg gtggtccctt    2100
acatatcatc atcacagtac agacagaaca atttgaccca acaacacta tcttacaatg    2160 ggtgggtgac catatttcaa cagacggcac tagttgtacc ccctggagcc ccatcgactt    2220
gccagttagt tgccaccgtg agtgcagcag ataactttgt tcttaggatt cccacagata    2280
ccacatattt tgctgattat cagggtgatg taaaagatgt tgtacaggca agcataaata    2340
ccaccttgca aaatgcacta aacacgagac cacagcagga acagtcatca aatggtataa    2400
tggttaatca aggggacgca cctgcattaa cagcggctga gactggtgag tctgatacta    2460
attctggtgg atcaacaatg gaacttcaag caacaaactg tgtgtttagc ctaagagaaa    2520
cagatttaga gtacctaatg tctagatatt cacttatgtt tgagggcact ttggattaca    2580
ctgatggggc tggcaaaagg catttgaggt atgatttgaa ttttagacaa attggcaaat    2640
caggtagtga tattaccaaa tttaaggctt ttacatactg gaggtttgat ttagatgctg    2700
tggtaatgat actggaggac aagcccgcag cagtgaggaa ccttatgttt cagattttgt    2760 ttaccccca tgggggtgct ataccctgta cacataactc ccagatttgg aatgctccta    2820
attcaaccag tatttacacc agagtaggaa attgtcctgc ctcgtttagg atacctttta    2880
tgtctgtttg caattattat acttcctttt atgatggtga tgggaattttt gatatgaatg    2940 gtgcgtctta tggtattaat ccaggtgatt ttataggcac aatatctatt aggatggcca    3000 atgactttt tactaatact accactggtt cctttagagc taagatcttt cttaggcctg    3060
taaatattga agcctatatg cctagacctc ttatttccta caaggctaat ggtgatgcca    3120
gacaagatag ttcacaatac taccctgcag cccagacggg ttttacccc gcggaacagc    3180 tgggacccta tgaaatttgc caaccagac atgcttcaga gctaattgat actaaatggg    3240
caagatactc ttgctcggtt aaatttgaca gaggttcatt tacagcatgg tttgtgggag    3300
aagacctgct tttggtaccc taccatgctg caaacaattg gagtcagaca acacatgtgt    3360
tcctgtggag agcatgggat aaggactgga gagaccatcc tgaattggaa atgaagatcc    3420
ccatttttga catgtggact gattctacca gagatgtcac ttttcttaaa ttggcctacg    3480
ctacaccata ctggttggag atgccagcaa aaggttctgc cataggtgat tacattgtag    3540
ttgtgaattc agcccacttc ccatggaaac agtactcagg cccaaaacca tttagacacc    3600
cctacttaca tattggacaa catacccaat acagactgtg gatgcatgct ggtgatgctg    3660
acaatggctt ctgtggagcc ggtttaatat ctagaggtaa actttatggt atagttacag    3720
caaggacaga ggctaaatca ggtggtacct atgtggccta cactgaactg gatgaagata    3780
ccttcctaca aacacaacaa agatgttttt attttggaat ggattcacac ttcaatcttg    3840
gaatgcatga ctgggtccag ggactcggcc aggtgttcgg agagggtgtt tctgggggagg    3900 tgaaaagaca agtggaagat tacttaggcc agatcaagcc cattattgat tcaggtacca    3960
```

```
ataaaattaa ggatgttatt aaagatgaaa tggttagtgc cagtatgtcc ttgttagtta      4020
aggtagttgc ttccctagta ctgtatatga attctaagga tgactgtaaa atgtccactt      4080
tagcttcatt gggtgcccct ttaggtgtag atatattttt gactgatcct attatgtacc      4140
tgtatagtaa gataactgga gaacctcaca gacaggggcc aacagagtgg cttaaagagt      4200
tcaatacagc cataaatgca tttaaaggat ttgatttcct ctgctccaaa ttaatgcaat      4260
tgattgaatg gattaaacag ttttccaga gggttgaacc agagtacaag gagtttaagg       4320
agttacttga atcttggccc aaagtttgtg ccaaagtgtt ggagtttaag aactgcaaaa      4380
caacactagg acaagaagat atttgtcaaa taaaggttta catagacaaa atgattgagt      4440
tgggaaacaa atatggccac aaatttcatt tacagatgtc tcagttactg caatgttcaa      4500
acataataaa caaagcttac agtaacatga caagatctag acatgaacct gttgcaattc      4560
ttatacatgg tgctcctgga actggaaagt cacttgctac agaaataatt ggtagggcaa      4620
tagcagataa gttagataat cagagaccct acacactccc accagacccc aaacattttg      4680
atggatataa tcaacagaaa gtggttatta tggatgattt aggacaaaac ccagatggtg      4740
aagattgcaa gatgttttgc cagatggtgt caaccactac ttacattcca cctatggcct      4800
ccttagatga gaaaggactt ccctttattt ctgactttgt tcttgcttct actaaccagc      4860
atgctttgac ccccagaact attgctgagc ctgatgctat taatagaaga tggtttatga      4920
atgtagatat tcaccttaag aaagaataca aggatgatag aggaaggtta gacatgtcaa      4980
agtgtttgcc ttgtaaagat tgcaaaccag tgaatttcag gagatgtaac ccattgattt      5040
gtggaaaagc catcatttta ctggacagga aacccagaa aaactggacc cttgattcag       5100
cagttagtta cttattggat gaatcagaga gaagaaaagg gttcttaaat gtagtggatg      5160
caatctttca gggacctgtg cagattccag aatgtgttag agaggatgaa ctgaaggaga      5220
agaaggtgaa ttcagagaga gacatccaag ctgatgtgat ggaattagtt agatgtacaa      5280
aatcccctgt tataattgag gaattagaga agcaggttt catcattcct gttgaggcag       5340
aagtgattag acagactagt aatgtgaata atgtaaccca aattatttca gcaactctag      5400
ctagtttggc agctataatt tctgtaggga ctgtagttta tttaatggtt aagttgtttt      5460
ccacaaaaca aggagcatac actggtgtgc ccaaaccaga aaccaagaga cctgtactta      5520
gaaaagcagt agtgcagggc ccagacatgg aatttgccaa gtcaattatg agatcaaatc      5580
tgtgtcaggt aaccaccagt gtgggaccct ttaccgggct gggcatctgt gataacatct      5640
tggtgctacc acgacatgct tatgtgagtg gaaacatagt gttagatggt atagacattc      5700
ctgtaacaga tgctgtagaa ttagaagcag aggagggaaa tttggaatta gtacagttaa      5760
cccttaagag aaatgaaaaa tttagggata ttagaaagtt tttaagtaat ggttttcaca      5820
gtgagaatga ttgctggttg tgcattaatt ctgagatgtt ttctaatgta tatatacctc      5880
ttaagagtgt ttctgccttt ggattcctta acctttctat gactcctact tacagaaacac     5940 ttgtttacaa ttaccctacc aagatgggac aatgtggtgg tgttgtgctg aaagcaggaa      6000 agatttagg catacatatt ggtggtgatg gaaccagagg gtttgcagcc ctactgaaga       6060
gagattactt tgtaaacaaa caaggtttga taacagagag atacacacca tcaagaccta      6120
ttaatgttag aacaaagaca gctttccaac cttctgtttt tcatgatgtc tttcctggga      6180
gtaaggaacc tgcagcaatg agtgtgcatg atccaagact tgaagtggat ctggaagaag      6240
caatatttgc aaagtacaaa ggcaatgttg acaccacact tccagaagaa gcacttatag      6300
caattgacca tttggttcc aaatttaagg caattgtacc agacaatctg tgtgagaaga      6360
```

-continued

```
tgtcattgga ggatgttgtc tatggtactg ataatctgga tggactagat ttaaccactt   6420
cagcaggtta cccctacaac accttgggga ttagaaagaa agatcttatt cctcccaaag   6480
gacagtctct ttcccctctt ataaaggctc ttgatcttta tggatatgat ttaccctta   6540
ctacttacat gaaggatgag ttgagaccaa aggagaaagt gaagatgggc aaaaccaggg   6600
tcattgagtg ttcatcactt aatgatacca taatgatgaa gcagactttt ggtcatctgt   6660
tccagacatg ccacaagaat cctggaacct acactggtgt agctgtaggc tgcaacccag   6720
atgtggattg gtcaaagttt gctgctgaga ttggtgatgc ctatgtgtgt gcttttgatt   6780
atacaaattg ggatgctagt ctgtcacctt tgtggtttga tgctttaaag ttgtttcttt   6840
ccaaactagg ttacagtggt agggatttag ttttgattga tcagttgtgt tattcaaatc   6900
acatttacaa gaataaggga tacaaagtta ccggcggtat gccatctggt tgctccggaa   6960
ctagtatctt taatagcatt attaacaata tagttattag gactttaata atgttagcat   7020
ataagaatat taatttagat gagttgttag ttttatgtta tggtgatgat ttattggttg   7080
cctatcccta tgaattagat ccaaatgtgc tggttccatt ggcaaagagt tatggtttga   7140
ccataacacc agcagacaaa tcaacaactt tccaaacagg aacaaagtta acagatgtta   7200
ccttcctgaa gaggggtttc aaattcgatg aggaataccc cttcctgtgt catcctgtat   7260
ttcctatgga ggaggtgcat gaatcaatta gatggaccaa gaatgccagc tatacccagg   7320
aacatgttac atcgctgtgt cttttggcat ggcacaatgg tgaggaggtt tatgaagagt   7380
tctgtacgaa aatcagatca gttccagtag gcagagctct catattacca ccttactctc   7440
agctgcgtag gtcttggtta gatatgtttt aggcggcgtg aacatatcag tgatacagga   7500
ttaacaatta ggctaattgg caatagaccc taagccgcct ataggg                  7546
```

<210> SEQ ID NO 2
<211> LENGTH: 7556
<212> TYPE: DNA
<213> ORGANISM: Porcine Sapelovirus

<400> SEQUENCE: 2

```
ggggtacatg cgtattacgg tacgcatgta ttccacactc atttcccccc tccaccctta     60
aggtggttgt atccccatac ctcaccctcc cttccacaca ggacggatac ttggacttgg    120
acccacggcg agaacatatg gtatggcttt tggatacgga tgaatggcag tagcgtggcg    180
agctatggaa aaatcgcaat tgtcgatagc catgttagtg acgcgcctcg gcgtgctcct    240
ttggtgattc ggcgactggt tacaggagag taggcagtga gctatgggca aacctctgca    300
gtattactca gagggaatgt gcaattgaga cttgacgagc gtctctttga gatgtggcgc    360
atgctcttgg cattacccata gtgagcttcc aggttgggaa acctggactg ggcctatact    420
acctgatagg gtcgcggctg gccgcctgta actagtatag tcagttgaaa ccccccatgg    480
aatctactac tactctttca ttttgcaact ggatccctaa gaaacagaga gcccgtgtgt    540
accttaccac cagtgtaaca cacgagaaat caagtggacc ctacacatat gtagtgtctg    600
acatgatcat gaaagaaaac agtagaacct cccttgctat ggctttcgta gaagggaaga    660
cacttgtgtt caacaccggc acacaattgg gacaagttca ttcagctaac acaggcaata    720
aacctcaagg agcatacaac catggctccg gtagtattac acaaataaac tactatggtt    780
ctgattactc ccaagcatgg aatcctacac aacagcaaat ggacccctcc cagttcacca    840
aaccagtgac tgaaatagcc aatgcaatgg caggaccatc tctcaaggca cctgacaagg    900
aagaagaagg gtacagtgat aggttaatgc aattgacagc aggaaactcc tgtataacaa    960
```

-continued

```
cacaagaagc agctaaagca gttgtagcat atggacaatg gccaagttat aacatagatg  1020
caggagaaca tctagatctt gctacaactc cagggacagc agtggacagg ttttacacct  1080
ttgacagctt aagatggacc gacacacaag tcggtgaatg gtctctgcca ctgcctggtg  1140
gtttgatgga cacaggcgtg tttggtcaaa acctaagatt ccactacctc tccaggatgg  1200
gcttttgtgt acatgtacag tgcaatgcat caaaattcca ccagggtgca ctcatagttg  1260
caatgatacc agagcatcaa acacctaccc aagtgagtaa cgggtttgag tatagaaatg  1320
gagtgaccta ccagggaaac aattatccaa ctgaacaact acctatattt ccacaccaga  1380
ttataaacct gaggaccaac aactctgcaa caatagtcta tccatatacc aattgtactc  1440
cagcaggatt tggtttagca cacaactttg tcaccctggt tattagggtt ttagtgccac  1500
tcaagtacaa tacaggtgct tcaactttg ttcctattac tgttagtgtg gccccaatgt  1560
gttcacagtt tgcaggattg agatcagcag taacaagaca gggttttcct gttaggcagg  1620
taccaggcag ccaacaattt atgacaacac aaagagatag tgggatacca atctacccag  1680
agtttcagaa aacccataat ttcaaattgc ccggaagggt aaccaatttg ctacaagttg  1740
ctcaggtggg gaccttttctc aaatttagta attctacaaa cgacaccaat agaatctatt  1800
tgaatttgga tattacacag ggtgaccagt catcaaggat ggtggctatt gatgttagca  1860
tggtttcagc ccacttgtcc accacatacc tttcacggtt ggcacagatg tatgccaatt  1920 acagggggttc tgttgttttt gagtttatgt tttgtggtag ccagatgcc actgggaaac  1980 tactgatagc atacacacct cctggtggca cttcccccac aactaggact gatgcaatgt  2040
tggcaacaca tgttatttgg gatataggtt tacagtccac atgtaaaatg gtggtccctt  2100
acatatcatc atcacagtac agacagaaca atttgaccca aacaacacta tcttacaatg  2160
ggtgggtgac catatttcaa cagacggcac tagttgtacc ccctggagcc ccatcgactt  2220
gccagttagt tgccaccgtg agtgcagcag ataactttgt tcttaggatt cccacagata  2280 ccacatatt tgctgattat cagggtgatg taaaagatgt tgtacaggca agcataaata  2340
ccaccttgca aaatgcactg aacacgagac cacagcagga acagtcatca aatggtataa  2400
tggttaatca aggggacgca cctgcattaa cagcggctga gactggtgag tctgatacta  2460
attctggtgg atcaacaatg gaacttcaag caacaaactg tgtgtttagc ctaagagaaa  2520
cagatttaga gtacctaatg tctagatatt cacttatgtt tgagggcact ttggattaca  2580
ctgatggggc tggcaaaagg catttgaggt atgatttgaa ttttagacaa attggcaaat  2640
caggtagtga tattaccaaa tttaaggctt ttacatactg gaggtttgat ttagatgctg  2700
tggtaatgat actggaggac aagcccgcag cagtgaggaa ccttatgttt cagattttgt  2760 ttaccccca tgggggtgct atacctggta catataactc ccagatttgg aatgctccta  2820
attcaaccag tatttacacc agagtaggaa attgtcctgc ctcgtttagg atacctttta  2880
tgtctgtttg caattattat acttcctttt atgatggtga tgggaatttt gatatgaatg  2940
gtgcgtctta tggtattaat ccaggtgatt ttataggcac aatatctatt aggatggcca  3000 atgactttt ttttactaat actaccactg gttcctttag agctaagatc tttcttaggc  3060
ctgtaaatat tgaagcctat atgcctagac ctcttatttc ctacaaggct aatggtgatc  3120
ccagacaaga tagttcacaa tactaccctg cagcccagac ggggttttac cccgcggaac  3180
agctgggacc ctatgaaatt tgccaaacca gacatgcttc agagctaatt gatactaaat  3240
gggcaagata ctcttgctcg gttaaatttg acagaggttc atttacagca tggtttgtgg  3300
gagaagacct gcttttggta ccctaccatg ctgcaaacaa ttggagtcag acaacacatg  3360
```

```
tgttcctgtg gagagcatgg gataaggact ggagagacca tcctgaattg gaaatgaaga    3420
tccccatttt ggacatgtgg actgattcta ccagagatgt cacttttctt aaattggcct    3480
acgctacacc atactggttg gagatgccag caaaaggttc tgccataggt gattacattg    3540
tagttgtgaa ttcagcccac ttcccatgga acagtactc aggcccaaaa ccatttagac     3600 accccctactt acatattgga caacataccc aatacagact gtggatgcat gctggtgatg   3660
ctgacaatgg cttctgtgga gccggtttaa tatctagagg taaacttat ggtatagtta    3720 cagcaaggac agaggctaaa tcaggtggta cctatgtggc ctacactgaa ctggatgaag    3780
ataccttcct acaaacacaa caaagatgtt ttgattttgg aatggattca cacttcaatc    3840
ttggaatgca tgactgggtc cagggactcg gccaggtgtt cggagagggt gtttctgggg    3900
aggtgaaaag acaagtggaa gattacttag ccagatcaa gcccattatt gattcaggta    3960
ccaataaaat taaggatgtt attaaagatg aaatggttag tgccagtatg tccttgttag    4020
ttaaggtagt tgcttcccta gtactgtata tgaattctaa ggatgactgt aaaatgtcca    4080
ctttagcttc attgggtgcc cttttaggtg tagatatatt tttgactgat cctattatgt    4140
acctgtatag taagatgact ggagaacctc acagacaggg gccaacagag tggcttaaag    4200
agttcaatac agccataaat gcatttaaag gatttgattt tctctgctcc aaattaatgc    4260
aattgattga atggattaaa cagttttttcc agagggttga accagagtac aaggagttta    4320
aggagttact tgaatcttgg cccaaagttt gtgccaaagt gttggagttt aagaactgca    4380
aaacaacact aggacaagaa gatatttgtc aaataaaggt ttacatagac aaaatgattg    4440
agttgggaaa caaatatggc cacaaatttc atttacagat gtctcagtta ctgcaatgtt    4500
caaacataat aaacaaagct tacagtaaca tgacaagatc tagacatgaa cctgttgcaa    4560
ttcttataca tggtgctcct ggaactggaa agtcacttgc tacagaaata attggtaggg    4620
caatagcaga taagttagat aatcagagac cttacacact cccaccagac cccaaacatt    4680
ttgatggata taatcaacag aaagtgggtta ttatggatga tttaggacaa acccagatg    4740 gtgaagattg caagatgttt tgccagatgg tgtcaaccac tacttacatt ccacctatgg    4800
cctccttaga tgagaaagga cttccccttta tttctgactt tgttcttgct tctactaacc    4860
agcatgcttt gacccccaga actattgctg agcctgatgc tattaataga agatggttta    4920
tgaatgtaga tattcacctt aagaaagaat acaaggatga tagaggaagg ttagacatgt    4980
caaagtgttt gccttgtaaa gattgcaaac cagtgaattt caggagatgt aacccattga    5040
tttgtggaaa agccatcatt ttactggaca ggaaaaccca gaaaaactgg acccttgatt    5100
cagcagttag ttacttattg gatgaatcag agagaagaaa agggttctta aatgtagtgg    5160
atgcaatctt tcagggacct gtgcagattc cagaatgtgt tagagaggat gaactgaaga    5220
ggaagaaggt gaattcagag agagacatcc aagctgatgt gatggaatta gttagatgta    5280
caaaatcccc tgttataatt gaggaattag agaaagcagg tttcatcatt cctgttgagg    5340
cagaagtgat tagacagact agtaatgtga ataatgtaac ccaaattatt tcagcaactc    5400
tagctagttt ggcagctata atttctgtag ggactgtagt ttatttaatg gttaagttgt    5460
tttccacaaa acaaggagca tacactggtg tgcccaaacc agaaaccaag agacctgtac    5520
ttagaaaagc agtagtgcag ggcccagaca tggaatttgc caagtcaatt atgagatcaa    5580
atctgtgtca ggtaaccacc agtgtgggac ctttaccgg gctgggcatc tgtgataaca    5640
tcttggtgct accacgacat gcttatgtga gtggaaacat agtgttagat ggtatagaca    5700
ttcctgtaac agatgctgta gaattagaag cagaggaggg aaatttggaa ttagtacagt    5760
```

```
taacccttaa gagaaatgaa aaatttaggg atattagaaa gttttttaagt aatggttttc    5820 acagtgagaa tgattgctgg ttgtgcatta attctgagat gttttctaat gtatatatac    5880
ctcttaagag tgtttctgcc tttggattcc ttaacctttc tatgactcct acttacagaa    5940
cacttgttta caattaccct accaagatgg gacaatgtgg tggtgttgtg ctgaaagcag    6000
gaaagatttt aggcatacat attggtggtg atggaaccag agggtttgca gccctactga    6060
agagagatta ctttgtaaac aaacaaggtt tgataacaga gagatacaca ccatcaaaac    6120
ctattaatgt tagaacaaag acagctttcc aaccttctgt ttttcatgat gtctttcctg    6180
ggagtaagga acctgcagca atgagtgtgc atgatccaag acttgaagtg gatctggaag    6240
aagcaatatt tgcaaagtac aaaggcaatg ttgacaccac acttccagaa gaagcactta    6300
tagcaattga ccatttggtt tccaaattta aggcaattgt accagacaat ctgtgtgaga    6360
agatgtcatt ggaggatgtt gtctatggta ctgataatct ggatggacta gatttaacca    6420
cttcagcagg ttaccctac aacaccttgg ggattagaaa gaaagatctt attcctccca    6480
aaggacagtc tctttcccct cttataaagg ctcttgatct ttatggatat gatttaccct    6540
ttactactta catgaaggat gagttgagac caaaggagaa agtgaagatg gcaaaacca    6600 gggtcattga gtgttcatca cttaatgata ccataatgat gaagcagact tttggtcatc    6660
tgttccagac atgccacaag aatcctggaa cctacactgg tgtagctgta ggctgcaacc    6720
cagatgtgga ttggtcaaag tttgctgctg agattggtga tgcctatgtg tgtgcttttg    6780
attatacaaa ttgggatgct agtctgtcac ctttgtggtt tgatgcttta aagttgtttc    6840
tttccaaact aggttacagt ggtagggatt tagttttgat tgatcagttg tgttattcaa    6900
atcacattta caagaataag ggatacaaag ttaccggcgg tatgccatct ggttgctccg    6960
gaactagtat ctttaatagc attattaaca atatagttat taggactta ataatgttag    7020 catataagaa tattaattta gatgagttgt tagttttatg ttatggtgat gatttattgg    7080
ttgcctatcc ctatgaatta gatccaaatg tgctggttcc attggcaaag agttatggtt    7140
tgaccataac accagcagac aaatcaacaa cttccaaac aggaacaaag ttaacagatg    7200
ttaccttcct gaagaggggt ttcaaattcg atgaggaata ccccttcctg tgtcatcctg    7260
tatttcctat ggaggaggtg catgaatcaa ttagatggac caagaatgcc agctatacc    7320 aggaacatgt tacatcgctg tgtctttgg catggcacaa tggtgaggag gtttatgaag    7380
agttctgtac gaaaatcaga tcagttccag taggcagagc tctcatatta ccaccttact    7440
ctcagctgcg taggtcttgg ttagatatgt tttaggcggc gtgaacatat cagtgataca    7500
ggattaacaa ttaggctaat tggcaataga ccctaagccg cctatagggt ctacaa        7556
```

UNITED STATES PATENT AND TRADEMARK OFFICE
CERTIFICATE OF CORRECTION

PATENT NO. : 11,124,777 B2  
APPLICATION NO. : 16/702287  
DATED : September 21, 2021  
INVENTOR(S) : Chen et al.

Page 1 of 1

It is certified that error appears in the above-identified patent and that said Letters Patent is hereby corrected as shown below:

In the Claims

In Claim 8, at Column 38, Lines 60-61:  
DELETE: "An immunogenic composition comprising a porcine sapelovirus (PSV) according to claim 1."  
INSERT: --An immunogenic composition comprising a porcine sapelovirus (PSV) according to claim 1, and a carrier.--

Signed and Sealed this  
Twenty-third Day of November, 2021

Drew Hirshfeld  
*Performing the Functions and Duties of the*  
*Under Secretary of Commerce for Intellectual Property and